(12) United States Patent
Rishel et al.

(10) Patent No.: US 7,910,738 B2
(45) Date of Patent: Mar. 22, 2011

(54) INTERMEDIATES FOR ALPHA-FLUOROALKYL TETRABENAZINE AND DIHYDROTETRABENAZINE IMAGING AGENTS AND PROBES

(75) Inventors: Michael James Rishel, Rensselaer, NY (US); Kande Kankanamalage Dayarathna Amarasinghe, Latham, NY (US); Sean Richard Dinn, Delmar, NY (US); Bruce Fletcher Johnson, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 688 days.

(21) Appl. No.: 11/947,275

(22) Filed: Nov. 29, 2007

(65) Prior Publication Data

US 2009/0143587 A1    Jun. 4, 2009

(51) Int. Cl.
*C07D 455/06* (2006.01)
(52) U.S. Cl. .......................................... 546/95
(58) Field of Classification Search ............... 546/95
See application file for complete search history.

(56) References Cited

U.S. PATENT DOCUMENTS

| 2,843,591 A | 7/1958 | Brossi et al. |
| 4,193,998 A | 3/1980 | Szantay et al. |
| 5,278,308 A | 1/1994 | Kung |

FOREIGN PATENT DOCUMENTS

| DE | 1068261 B1 | 11/1959 |
| WO | WO9316730 A1 | 9/1993 |
| WO | WO2005077946 A1 | 8/2005 |
| WO | WO2007005283 A2 | 1/2007 |
| WO | WO2007130365 A2 | 11/2007 |
| WO | WO2008154243 A1 | 12/2008 |

OTHER PUBLICATIONS

Goswami et al. Nuclear Medicine and Biology, 33, 2006, 685-694.*
Popp et al., "Synthesis of Potential Antineoplastic Agents XXVI: 1,3,4,6,7,11b-Hexahydro-9,10-dimethoxy-2H-benso[a]2-quinolizinone Derivatives", Journal of Pharmaceutical Sciences, vol. 67, No. 6, pp. 871-873, XP-002513807, Jun. 1978.
PCT International Search Report dated Feb. 18, 2009.
PCT International Search Report dated Apr. 3, 2009.
Zheng et al., "Computational Neural Network Analysis of the Affinity of Lobeline and Tetrabenazine Analogs for the Vesicular Monoamine Transporter-2", Bioorganic & Medicinal Chemistry, vol. 15, pp. 2975-2992, 2007.
Kung et al., "Characterization of Optically Resolved 9-Fluoropropyl-Dihydrotetrabenzaine as a Potential PET Imaging Agent Targeting Vesicular Monoamine Transporters", Nuclear Medicine and Biology, vol. 34, pp. 239-246, 2007.
Goswami et al., "Fluoroalkyl Derivatives of Dihydrotetrabenazine as Positron Emission Tomography Imaging Agents Targeting Vesicular Monoamine Transporters", Nuclear Medicine and Biology, vol. 33, pp. 685-694, 2006.
Kilbourn et al., "Pharmacokinetics of [18F]Fluoroalkyl Derivatives of Dihydrotetrabenazine in Rate and Monkey Brain", Nuclear Medicine and Biology, vol. 34, pp. 233-237, 2007.

* cited by examiner

*Primary Examiner* — Nizal S Chandrakumar
(74) *Attorney, Agent, or Firm* — Andrew J. Caruso

(57) ABSTRACT

The present invention provides novel fluorophilic compounds having structure VII

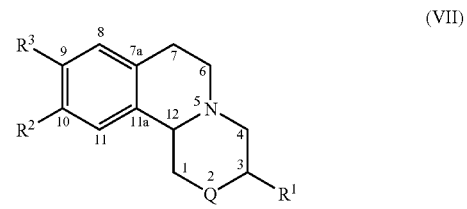

wherein Q is a carbonyl group, a protected carbonyl group, a hydroxy methine group, or a protected hydroxy methine group; $R^1$ is a $C_1$-$C_{20}$ aliphatic, $C_2$-$C_{20}$ cycloaliphatic, or $C_2$-$C_{20}$ aromatic radical comprising at least one functional group susceptible to reaction with nucleophilic fluoride ion or an electrophilic fluorinating agent; $R^2$ is hydrogen or a $C_1$-$C_{10}$ aliphatic radical; and $R^3$ is hydrogen or a $C_1$-$C_{10}$ aliphatic radical. The fluorophilic compounds are provided in both racemic and enantiomerically enriched forms and are useful as intermediates in the preparation of novel PET imaging agents and probes useful in the discovery and performance assessment of PET imaging agents. The fluorophilic compounds are particularly useful in the preparation of PET imaging agents and probes having a high affinity for VMAT-2, a biomarker implicated in human diabetes and other illnesses such as Parkinson's disease.

19 Claims, No Drawings

INTERMEDIATES FOR ALPHA-FLUOROALKYL TETRABENAZINE AND DIHYDROTETRABENAZINE IMAGING AGENTS AND PROBES

CROSS REFERENCE TO RELATED APPLICATIONS

This application is related to U.S. patent application Ser. Nos. 11/760,359, and 11/760,372 filed Jun. 8, 2007, and U.S. patent application Ser. Nos. 11/923,926 and 11/923,805 filed Oct. 25, 2007.

BACKGROUND

This invention relates to alpha-fluoroalkyl compounds related to tetrabenazine and dihydrotetrabenazine and intermediates useful in the preparation of such alpha-fluoroalkyl compounds.

Since first reported on in 1957 (Pletscher, A. (1957) Release of 5-hydroxytryptamine by benzoquinolizine derivatives with sedative action, *Science* 126, 507), tetrabenazine and structurally related compounds have been widely investigated, and a number of TBZ compounds and derivatives of tetrabenazine have shown promise in the treatment of a variety of conditions affecting human health. For example, dihydrotetrabenazine has been identified as an agent for the treatment of schizophrenia and other psychoses (See for example WO 2007017654 A1), and tetrabenazine has shown promise as an agent in the treatment of Huntington's disease (Neurology (2006), 66(3), 366-372). Although most preparations used in biological studies of tetrabenazine and its derivatives have been carried out on racemates, in at least one instance the biological activity exhibited by enantiomers tested separately was highly differentiated (See Koeppe, R. A. et al. (1999) Assessment of extrastriatal vesicular monoamine transporter binding site density using stereoisomers of [11C]dihydrotetrabenazine, *J Cereb Blood Flow Metab* 19, 1376-1384).

More recently, derivatives of 9-desmethyl (±)-dihydrotetrabenazine incorporating a fluorine-18 atom have been shown to be useful as PET imaging agents, *Nuclear Medicine and Biology* 33 (2006) 685-694. See also *Nuclear Medicine and Biology* 34 (2007) 239-246; and *Nuclear Medicine and Biology* 34 (2007) 233-237.

The present invention provides both a new class of fluorinated tetrabenazine and dihydrotetrabenazine derivatives and fluorinated tetrabenazine and dihydrotetrabenazine analogs, and discloses efficient synthetic methodology which may be used to prepare such compounds in enantiomerically enriched or racemic forms. The alpha-fluoroalkyl tetrabenazine and dihydrotetrabenazine compounds provided by the present invention are useful as PET imaging agents, probes for the development of PET imaging agents, and therapeutic agents. In addition, the present invention provides novel synthetic intermediate compositions which may be used to prepare either or both enantiomers of the subject tetrabenazine and dihydrotetrabenazine derivatives and tetrabenazine and dihydrotetrabenazine analogs.

BRIEF DESCRIPTION

In one embodiment, the present invention provides a fluorophilic compound having structure VII

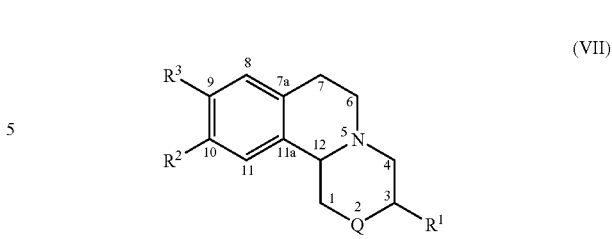

wherein Q is a carbonyl group, a protected carbonyl group, a hydroxy methine group, or a protected hydroxy methine group; $R^1$ is a $C_1$-$C_{20}$ aliphatic, $C_2$-$C_{20}$ cycloaliphatic, or $C_2$-$C_{20}$ aromatic radical comprising at least one functional group susceptible to reaction with nucleophilic fluoride ion or an electrophilic fluorinating agent; $R^2$ is hydrogen or a $C_1$-$C_{10}$ aliphatic radical; and $R^3$ is hydrogen or a $C_1$-$C_{10}$ aliphatic radical.

In another embodiment, the present invention provides an enantiomerically enriched fluorophilic compound comprising a principal component enantiomer having structure VIII

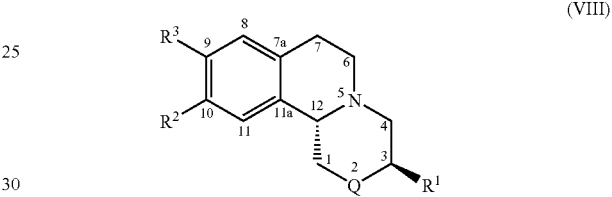

wherein Q is a carbonyl group, a protected carbonyl group, a hydroxy methine group, or a protected hydroxy methine group; $R^1$ is a $C_1$-$C_{20}$ aliphatic, $C_2$-$C_{20}$ cycloaliphatic, or $C_2$-$C_{20}$ aromatic radical comprising at least one functional group susceptible to reaction with nucleophilic fluoride ion or an electrophilic fluorinating agent; $R^2$ is hydrogen or a $C_1$-$C_{10}$ aliphatic radical; and $R^3$ is hydrogen or a $C_1$-$C_{10}$ aliphatic radical.

In yet another embodiment, the present invention provides an enantiomerically enriched fluorophilic compound comprising a principal component enantiomer having structure IX

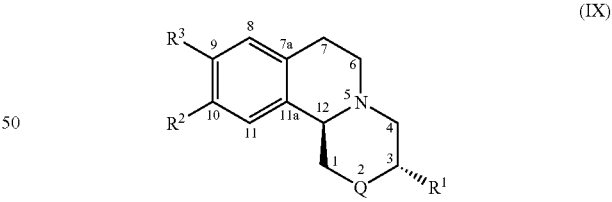

wherein Q is a carbonyl group, a protected carbonyl group, a hydroxy methine group, or a protected hydroxy methine group; $R^1$ is a $C_1$-$C_{20}$ aliphatic, $C_2$-$C_{20}$ cycloaliphatic, or $C_2$-$C_{20}$ aromatic radical comprising at least one functional group susceptible to reaction with nucleophilic fluoride ion or an electrophilic fluorinating agent; $R^2$ is hydrogen or a $C_1$-$C_{10}$ aliphatic radical; and $R^3$ is hydrogen or a $C_1$-$C_{10}$ aliphatic radical.

DETAILED DESCRIPTION

In the following specification and the claims, which follow, reference will be made to a number of terms, which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "solvent" can refer to a single solvent or a mixture of solvents.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC($CF_3)_2$PhO—), 4-chloromethylphen-1-yl, 3-trifluorovinyl-2-thienyl, 3-trichloromethylphen-1-yl (i.e., 3-CCl$_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2)_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis (phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}$C(CF$_3)_2$$C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., CH$_3$CHBrCH$_2$C$_6$H$_{10}$O—), and the like. Further examples of cycloaliphatic radicals include 4-allyloxycyclohex-1-yl, 4-aminocyclohex-1-yl (i.e., H$_2$NC$_6$H$_{10}$—), 4-aminocarbonylcyclopent-1-yl (i.e., NH$_2$COC$_5$H$_8$—), 4-acetyloxycyclohex-1-yl, 2,2-dicyanoisopropylidenebis(cyclohex-4-yloxy) (i.e., —OC$_6$H$_{10}$C(CN)$_2$C$_6$H$_{10}$O—), 3-methylcyclohex-1-yl, methylenebis(cyclohex-4-yloxy) (i.e., —OC$_6$H$_{10}$CH$_2$C$_6$H$_{10}$O—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —OC$_6$H$_{10}$(CH$_2)_6$C$_6$H$_{10}$O—), 4-hydroxymethylcyclohex-1-yl (i.e., 4-HOCH$_2$C$_6$H$_{10}$—), 4-mercaptomethylcyclohex-1-yl (i.e., 4-HSCH$_2$C$_6$H$_{10}$—), 4-methylthiocyclohex-1-yl (i.e., 4-CH$_3$SC$_6$H$_{10}$—), 4-methoxycyclohex-1-yl, 2-methoxycarbonylcyclohex-1-yloxy (2-CH$_3$OCOC$_6$H$_{10}$O—), 4-nitromethylcyclohex-1-yl (i.e., NO$_2$CH$_2$C$_6$H$_{10}$—), 3-trimethylsilylcyclohex-1-yl, 2-t-butyldimethylsilylcyclopent-1-yl, 4-trimethoxysilylethylcyclohex-1-yl (e.g., (CH$_3$O)$_3$SiCH$_2$CH$_2$C$_6$H$_{10}$—), 4-vinylcyclohexen-1-yl, vinylidenebis (cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl (C₄H₇O—) represents a C₄ cycloaliphatic radical. The cyclohexylmethyl radical (C₆H₁₁CH₂—) represents a C₇ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —CH₂CHBrCH₂—), and the like. Further examples of aliphatic radicals include allyl, aminocarbonyl (i.e., —CONH₂), carbonyl, 2,2-dicyanoisopropylidene (i.e., —CH₂C(CN)₂CH₂—), methyl (i.e., —CH₃), methylene (i.e., —CH₂—), ethyl, ethylene, formyl (i.e., —CHO), hexyl, hexamethylene, hydroxymethyl (i.e., —CH₂OH), mercaptomethyl (i.e., —CH₂SH), methylthio (i.e., —SCH₃), methylthiomethyl (i.e., —CH₂SCH₃), methoxy, methoxycarbonyl (i.e., CH₃OCO—), nitromethyl (i.e., —CH₂NO₂), thiocarbonyl, trimethylsilyl (i.e., (CH₃)₃Si—), t-butyldimethylsilyl, 3-trimethyoxysilylpropyl (i.e., (CH₃O)₃SiCH₂CH₂CH₂—), vinyl, vinylidene, and the like. By way of further example, a $C_1$-$C_{10}$ aliphatic radical contains at least one but no more than 10 carbon atoms. A methyl group (i.e., CH₃—) is an example of a $C_1$ aliphatic radical. A decyl group (i.e., CH₃(CH₂)₉—) is an example of a $C_{10}$ aliphatic radical.

As noted, in one embodiment the present invention provides an alpha-fluoroalkyl tetrabenazine compound having structure I

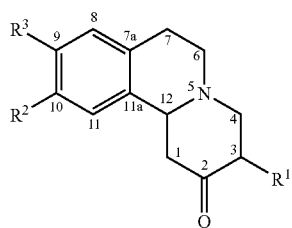

wherein $R^1$ is a $C_1$-$C_{10}$ fluorinated aliphatic radical; $R^2$ is hydrogen or a $C_1$-$C_{10}$ aliphatic radical; and $R^3$ is hydrogen or a $C_1$-$C_{10}$ aliphatic radical.

As noted, in another embodiment the present invention provides an alpha-fluoroalkyl dihydrotetrabenazine compound having structure IV

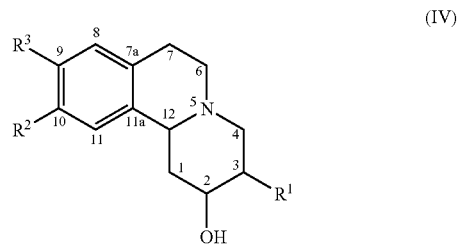

wherein $R^1$ is a $C_1$-$C_{10}$ fluorinated aliphatic radical; $R^2$ is hydrogen or a $C_1$-$C_{10}$ aliphatic radical; and $R^3$ is hydrogen or a $C_1$-$C_{10}$ aliphatic radical.

The alpha-fluoroalkyl tetrabenazine and dihydrotetrabenazine compounds I and IV provided by the present invention are shown herein to possess a high affinity for Type 2 Vesicular Monoamine Transporters (VMAT-2), a group of biomarkers which are believed to correlate with diabetic activity in human patients. The discovery that substitution by fluorine is tolerated with respect to VMAT-2 binding in this series of novel alpha-fluoroalkyl tetrabenazine and dihydrotetrabenazine compounds enables the compounds of present invention to be used as positron emission tomography (PET) imaging agents in studies targeting the VMAT-2 biomarker.

Thus, in one embodiment, the present invention provides radiolabeled alpha-fluoroalkyl tetrabenzine compounds falling within the scope of generic structure I comprising a fluorine-18 atom. In an alternate embodiment, the present invention provides radiolabeled alpha-fluoroalkyl dihydrotetrabenazine compounds falling within the scope of generic structure IV comprising a fluorine-18 atom. Fluorine-18 labeled alpha-fluoroalkyl tetrabenzine compounds I and alpha-fluoroalkyl dihydrotetrabenzine compounds IV are suitable for use as imaging agents for positron emission tomography (PET) screening of human patients for pathological conditions related to diabetes. Positron emission tomography has become a medical imaging technique of critical importance to human health.

In an alternate embodiment, the present invention provides alpha-fluoroalkyl tetrabenazine and dihydrotetrabenazine compounds falling within the scope of either generic structure I or IV and comprising a fluorine-19 atom, a stable isotope of fluorine. The alpha-fluoroalkyl compounds comprising a fluorine-19 atom are useful in binding studies which allow the identification of those alpha-fluoroalkyl compounds possessing optimal affinity for a target biomarker, for example VMAT-2. A substantial binding affinity of a given fluorine-19 containing alpha-fluoroalkyl tetrabenzine or dihydrotetrabenazine compound for a target biomarker such as VMAT-2 is a reliable predictor of utility in PET imaging of the corresponding fluorine-18 containing alpha-fluoroalkyl compound. As is disclosed herein, alpha-fluoroalkyl tetrabenazine and dihydrotetrabenazine compounds I and IV show substantial binding affinity for the biomarker VMAT-2.

Although throughout this disclosure there is considerable focus on human health, the alpha-fluoroalkyl tetrabenazine and dihydrotetrabenazine compounds provided by the present invention are useful in the study and treatment of a variety of human and animal diseases as imaging agents, as probes for the development of imaging agents, and as therapeutic agents.

Alpha-fluoroalkyl tetrabenazine compounds having structure I are illustrated in Table 1 below.

TABLE 1

Examples of Alpha-Fluoroalkyl Tetrabenazines Having Structure I

| Entry | R¹ | R² | R³ | Ring Position* Stereochemistry RP-3 | RP-12 |
|---|---|---|---|---|---|
| 1a | ~CH₂CH₂-$^{19}$F | CH₃ | CH₃ | R/S | R/S |
| 1b | ~CH₂CH₂-$^{18}$F | CH₃ | CH₃ | R | R |
| 1c | ~CH₂CH₂CH₂-$^{19}$F | CH₃O | CH₃O | R/S | R/S |
| 1d | ~CH₂CH₂CH₂-$^{18}$F | CH₃O | CH₃O | S | S |
| 1e | ~(CH₂)₃-$^{19}$F | EtO | CH₃O | S | R |
| 1f | ~(CH₂)₃-$^{18}$F | EtO | EtO | R | S |
| 1g | ~CH₂-O-CH₂CH₂-$^{19}$F (CH₃CH₂) | CH₃CH₂ | R/S | R/S |
| 1h | ~CH₂-O-CH₂CH₂-$^{18}$F (CH₃O) | CH₃O | R | R |
| 1i | ~CH(OH)CH₂-$^{18}$F | CH₃O | CH₃O | R/S | R/S |
| 1j | ~CH($^{18}$F)CH₂-$^{18}$F | CH₃O | CH₂CH₃ | R/S | R/S |
| 1k | ~C(=O)CH₂-$^{18}$F | CH₃O | H | R | R |

*RP-3 = Ring position-3, RP-12 = Ring position-12

In general, and throughout this disclosure, where no absolute or relative stereochemistry is shown for a structure, as in for example structure I, the structure is intended to encompass all possible absolute and relative stereochemical configurations. Thus, structure I depicts an alpha-fluoroalkyl tetrabenazine compound in which no absolute or relative stereochemistry is shown. As such, structure I is intended to represent a genus of alpha-fluoroalkyl tetrabenazine compounds which includes the racemic compound 1a (Table 1) having both the R configuration and S configuration at ring positions-3 and 12. In another embodiment, structure I represents alpha-fluoroalkyl tetrabenazine compound 1b (Table 1) having the R configuration (absolute stereochemistry) at ring positions-3 and 12. In yet another embodiment, structure I represents compound 1d (Table 1) having absolute stereochemistry opposite that of compound 1b. Those having ordinary skill in the art will appreciate that the individual alpha-fluoroalkyl tetrabenazine compounds shown in Table 1 herein are illustrative of tetrabenazine (TBZ) derivatives falling within the scope of generic structure I.

As noted, in one embodiment, the present invention provides an alpha-fluoroalkyl tetrabenzine compound having structure I which may be a racemic mixture (e.g. compound 1a (Table 1), a single enantiomer (e.g. compound 1b (Table 1), or a composition enantiomerically enriched in a single principal component enantiomer. Entries 2a-2c in Table 2 below illustrate alpha-fluoroalkyl tetrabenazine compounds I comprising a principal component enantiomer and at least one minor component enantiomer.

TABLE 2

Alpha-fluoroalkyl Tetrabenzine Compounds I Comprising A Principal Component Enantiomer And At Least One Minor Component Enantiomer.

| Entry | Structure of Principal Component Enantiomer | Structure of Minor Component Enantiomer |
|---|---|---|
| 2a | [H₃CO-, H₃CO- substituted tetrabenazine with R at position 12, R at position 3, CH₂-$^{18}$F side chain] 95 mole % | [H₃CO-, H₃CO- substituted tetrabenazine with S at position 12, S at position 3, CH₂-$^{18}$F side chain] |

TABLE 2-continued

Alpha-fluoroalkyl Tetrabenzine Compounds I Comprising A Principal
Component Enantiomer And At Least One Minor Component Enantiomer.

| Entry | Structure of Principal Component Enantiomer | Structure of Minor Component Enantiomer |
|---|---|---|
| 2b | EtO-... (12R, 3R) 98 mole % | EtO-... (12S, 3S) |
| 2c | butyl-... (12S, 3S) 88 mole % | butyl-... (12R, 3R) |

In Table 2 the alpha-fluoroalkyl tetrabenazine compositions comprise a principal component enantiomer (the structures appearing under the title heading "Structure of Principal Component Enantiomer") and a "Minor Component Enantiomer". In the alpha-fluoroalkyl tetrabenazine compositions illustrated in Table 2 the mole percentage of the principal component enantiomer is given as "mole %" and refers to the mole percentage of the principal component enantiomer having the structure shown relative to the amounts of all other alpha-fluoroalkyl tetrabenazine components in the composition. For the purposes of this discussion an alpha-fluoroalkyl tetrabenazine is any compound falling within the scope of generic structure I. Entry 2a represents an alpha-fluoroalkyl tetrabenazine composition comprising 95 mole % of the R, R principal component enantiomer shown and a lesser amount of the S, S minor component enantiomer. Entry 2c represents an alpha-fluoroalkyl tetrabenazine composition comprising 88 mole percent of the S, S principal component enantiomer having the structure shown and a lesser amount of the R, R minor component enantiomer. Those skilled in the art will appreciate that the tetrabenazine and dihydrotetrabenazine compositions provided by the present invention may comprise a principal component enantiomer, a minor component enantiomer, and additional diastereomeric tetrabenazine or dihydrotetrabenazine components. In one embodiment, the present invention provides an alpha-fluoroalkyl tetrabenazine composition comprising a principal component enantiomer and related diastereomers. In an alternate embodiment, the present invention provides an alpha-fluoroalkyl tetrabenazine composition having no principal component enantiomer and which is a diastereomeric mixture.

In one embodiment, the present invention provides an alpha-fluoroalkyl tetrabenazine compound represented by structure I which is enantiomerically enriched and is comprised of at least 95 mole percent (mole %) of an enantiomer having the R configuration at ring position-12.

In an alternate embodiment, the present invention provides an alpha-fluoroalkyl tetrabenazine compound represented by structure I which is enantiomerically enriched and is comprised of at least 95 mole percent (mole %) of an enantiomer having the R configuration at ring position-3.

In one embodiment, the present invention provides an alpha-fluoroalkyl tetrabenazine compound having structure I in which the fluorinated aliphatic radical at ring position-3 (—$R^1$) has a syn-configuration relative to the hydrogen at ring position-12. The principal component enantiomers of Entries 2a-2c of Table 2 illustrate alpha-fluoroalkyl tetrabenazine compounds in which the fluorinated aliphatic moiety at ring position-3 (—$R^1$) has a syn-configuration relative to the hydrogen at ring position-12.

In one embodiment, the present invention provides an enantiomerically enriched alpha-fluoroalkyl tetrabenazine compound comprising a principal component enantiomer having structure II

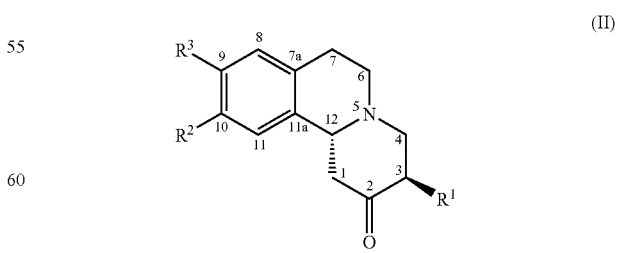

(II)

wherein $R^1$ is a $C_1$-$C_{10}$ fluorinated aliphatic radical; $R^2$ is hydrogen or a $C_1$-$C_{10}$ aliphatic radical; and $R^3$ is hydrogen or a $C_1$-$C_{10}$ aliphatic radical.

Principal component enantiomers having structure II are illustrated in Table 3 below.

TABLE 3

Principal Component Enantiomers Having Structure II

| Entry | Structure |
|---|---|
| 3a | H₃CO-, CH₃CH₂O- substituted tetrabenazine with ¹⁹F-propyl group |
| 3b | H₃C-CH₂- substituted tetrabenazine with ¹⁸F-ethyl group |
| 3c | H₃C-, H₃C- substituted tetrabenazine with ¹⁸F-methylene-allyl group |

In one embodiment, the present invention provides an enantiomerically enriched alpha-fluoroalkyl tetrabenazine compound comprising at least 80 mole percent of an enantiomer having structure II, for example the composition comprising the compound of Entry 3a (Table 3) wherein the R, R enantiomer shown represents at least 80 mole percent relative to the amounts of all other alpha-fluoroalkyl tetrabenazine components in the composition.

In an alternate embodiment, the present invention provides an enantiomerically enriched alpha-fluoroalkyl tetrabenazine compound which is comprised of at least 95 mole % of an enantiomer having structure II, for example an alpha-fluoroalkyl tetrabenazine composition comprising the compound of Entry 3b (Table 3) wherein the R, R enantiomer shown represents at least 95 mole percent relative to the amounts of all other alpha-fluoroalkyl tetrabenazine components in the composition.

In one embodiment, the present invention provides an enantiomerically enriched alpha-fluoroalkyl tetrabenazine compound comprising a principal component enantiomer having structure II wherein $R^1$ is a $C_5$-$C_{10}$ fluorinated aliphatic radical; and $R^2$ and $R^3$ are methoxy groups and which are illustrated in Table 4 below.

TABLE 4

Principal Component Enantiomers Having Structure II
Wherein $R^1$ Is A $C_5$-$C_{10}$ Fluorinated Aliphatic
Radical And $R^2$ And $R^3$ Are Methoxy Groups

| Entry | Structure |
|---|---|
| 4a | H₃CO-, H₃CO- substituted tetrabenazine with -CH₂CH₂C(CH₃)₂CH₂¹⁹F group |
| 4b | H₃CO-, H₃CO- substituted tetrabenazine with -CH₂CH₂C(CH₃)₂CH₂¹⁸F group |

TABLE 4-continued

Principal Component Enantiomers Having Structure II
Wherein $R^1$ Is A $C_5$-$C_{10}$ Fluorinated Aliphatic
Radical And $R^2$ And $R^3$ Are Methoxy Groups

| Entry | Structure |
|---|---|
| 4c | (structure) |
| 4d | (structure) |

In one embodiment, the present invention provides an enantiomerically enriched alpha-fluoroalkyl compound comprising a principal component enantiomer having structure III

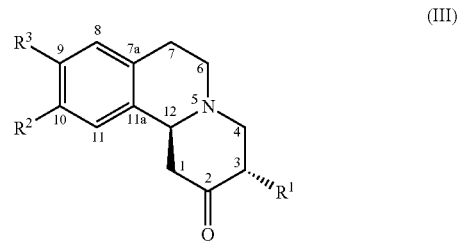

(III)

wherein $R^1$ is a $C_1$-$C_{10}$ fluorinated aliphatic radical; $R^2$ is hydrogen or a $C_1$-$C_{10}$ aliphatic radical; and $R^3$ is hydrogen or a $C_1$-$C_{10}$ aliphatic radical.

Principal component enantiomers having structure III are illustrated in Table 5 below.

TABLE 5

Principal Component Enantiomers Having Structure III

| Entry | Structure |
|---|---|
| 5a | (structure) |
| 5b | (structure) |
| 5c | (structure) |

In one embodiment, the present invention provides an enantiomerically enriched alpha-fluoroalkyl tetrabenazine compound comprising at least 80 mole percent of an enantiomer having structure III, for example an alpha-fluoroalkyl tetrabenazine composition comprising the compound of Entry 5a (Table 5) wherein the S, S enantiomer shown represents at least 80 mole percent relative to the amounts of all other alpha-fluoroalkyl tetrabenazine components in the composition. In another embodiment, the present invention provides an enantiomerically enriched alpha-fluoroalkyl tetrabenazine compound comprising at least 95 mole percent of an enantiomer having structure III, for example an alpha-fluoroalkyl tetrabenazine composition comprising the compound of Entry 5b (Table 5) wherein the S, S enantiomer shown represents at least 95 mole percent relative to the amounts of all other alpha-fluoroalkyl tetrabenazine components in the composition.

In another embodiment, the present invention provides an enantiomerically enriched alpha-fluoroalkyl compound comprising a principal component enantiomer having structure III wherein $R^1$ is a $C_5$-$C_{10}$ fluorinated aliphatic radical; and $R^2$ and $R^3$ are methoxy groups, and which are illustrated in Table 6 below.

TABLE 6

Principal Component Enantiomers Having Structure III Wherein $R^1$ Is A $C_5$-$C_{10}$ Fluorinated Aliphatic Radical; And $R^2$ And $R^3$ Are Methoxy Groups

| Entry | Structure |
|---|---|
| 6a | 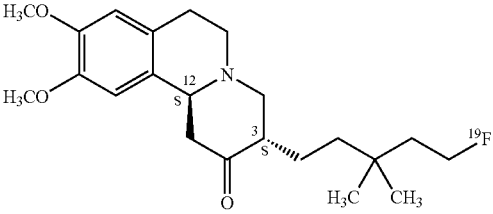 |
| 6b | 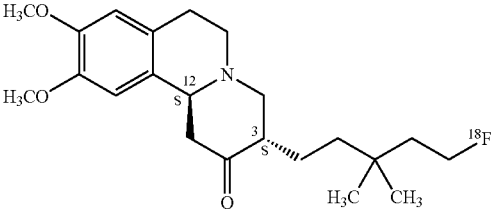 |
| 6c | 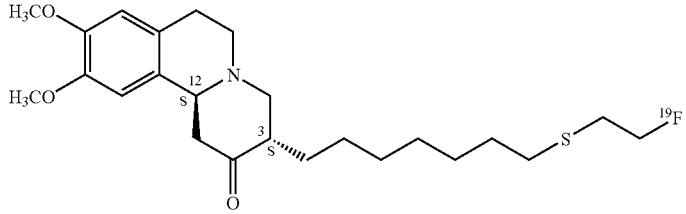 |
| 6d | 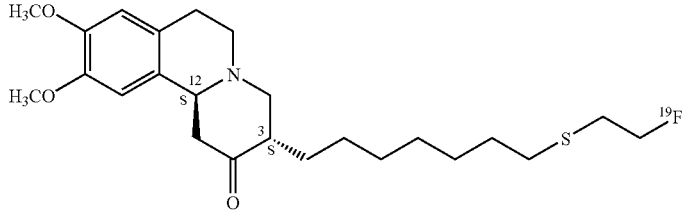 |

As noted the present invention provides novel alpha-fluoroalkyl tetrabenazine compounds I, novel alpha-fluoroalkyl dihydrotetrabenazine compounds IV, and in certain embodiments, mixtures thereof. Alpha-fluoroalkyl dihydrotetrabenazine compounds having structure IV are illustrated in Table 7 below.

TABLE 7

Examples of Alpha-Fluoroalkyl Dihydrotetrabenazines Having Structure IV

| Entry | $R^1$ | $R^2$ | $R^3$ | Ring Position Stereochemistry | | |
|---|---|---|---|---|---|---|
| | | | | RP-2 | RP-3 | RP-12 |
| 7a | ~~~~$^{19}$F | $CH_3$ | $CH_3$ | R/S | R/S | R/S |
| 7b | ~~~~$^{18}$F | $CH_3$ | $CH_3$ | R | R | R |
| 7c | ~~~~$^{19}$F | $CH_3O$ | $CH_3O$ | R/S | R/S | R/S |
| 7d | ~~~~$^{18}$F | $CH_3O$ | $CH_3O$ | R/S* | R | R |
| 7e | ~~~~$^{19}$F | EtO | $CH_3O$ | R/S* | S | S |
| 7f | ~~~~$^{18}$F | EtO | EtO | S | S | S |
| 7g | ~~~~O~~~~$^{19}$F | $CH_3CH_2$ | $CH_3CH_2$ | R/S | R/S | R/S |
| 7h | ~~~~O~~~~$^{18}$F | $CH_3O$ | $CH_3O$ | R | R | R |
| 7i | $^{18}$F / $^{18}$F | $CH_3O$ | $CH_2CH_3$ | R/S | R/S | R/S |
| 7j | O / $^{18}$F | $CH_3O$ | H | R/S | R/S | R |

*Diastereomeric mixture with ring position-2 being epimeric

Structure IV represents a genus of alpha-fluoroalkyl dihydrotetrabenazine compounds which includes the racemic compound 7a (Table 7) having both the R configuration and S configuration at ring positions-2, 3 and 12. In another embodiment, structure IV represents alpha-fluoroalkyl dihydrotetrabenazine compound 7b (Table 7) having the R configuration (absolute stereochemistry) at ring positions-2, 3 and 12. In yet another embodiment, structure IV represents compound 7f (Table 7) having absolute stereochemistry opposite that of compound 7b. Those having ordinary skill in the art will appreciate that the individual alpha-fluoroalkyl dihydrotetrabenazine compounds shown in Table 7 herein are illustrative of dihydrotetrabenazine (DTBZ) derivatives falling within the scope of generic structure IV. Those skilled in the art will appreciate as well that alpha-fluoroalkyl dihydrotetrabenazine compounds 7d and 7e represent diastereomeric mixtures.

As noted, in one embodiment, the present invention provides an alpha-fluoroalkyl dihydrotetrabenzine compound having structure IV which may be a racemic mixture (e.g. compound 7a (Table 7), a single enantiomer (e.g. compound 7b (Table 7), or a composition enantiomerically enriched in a single principal component enantiomer. Entries 8a-8c in Table 8 below illustrate alpha-fluoroalkyl dihydrotetrabenazine compounds IV comprising a principal component enantiomer and at least one minor component enantiomer.

In Table 8 the alpha-fluoroalkyl dihydrotetrabenazine compositions comprise a principal component enantiomer and a minor component enantiomer. In the alpha-fluoroalkyl dihydrotetrabenazine compositions illustrated in Table 8 the mole percentage of the principal component enantiomer is given as "mole %" and refers to the mole percentage of the principal component enantiomer having the structure shown relative to the amounts of all other alpha-fluoroalkyl dihydrotetrabenazine components in the composition. For the purposes of this discussion an alpha-fluoroalkyl dihydrotetrabenazine is any compound falling within the scope of generic structure IV. Entry 8a represents an alpha-fluoroalkyl dihydrotetrabenazine composition comprising 98 mole % of the R, R, R principal component enantiomer shown and a lesser amount of the S, S, S minor component enantiomer. Entry 8c represents an alpha-fluoroalkyl dihydrotetrabenazine composition comprising 88 mole percent of the S, S, S principal component enantiomer having the structure shown and a lesser amount of the R, R, R minor component enantiomer. Entry 8b represents a pair of diastereomers comprising the R, S, R-enantiomer shown as the principal component enantiomer, and a minor component S, S, S-enantiomer.

In one embodiment, the present invention provides an alpha-fluoroalkyl dihydrotetrabenazine compound represented by structure IV which is enantiomerically enriched

TABLE 8

Alpha-fluoroalkyl Dihydrotetrabenzine Compounds IV Comprising A
Principal Component Enantiomer And At Least One Minor Component Enantiomer.

| Entry | Structure of Principal Component Enantiomer | Structure of Minor Component Enantiomer |
|---|---|---|
| 8a | 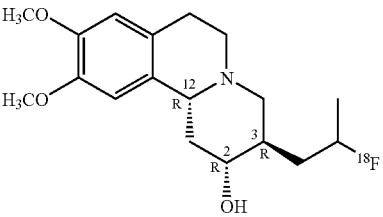<br>98 mole % | 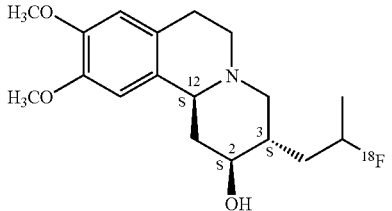 |
| 8b | 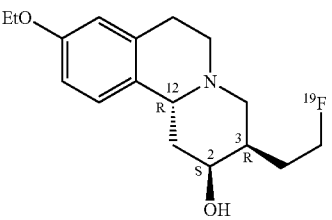<br>72 mole % | 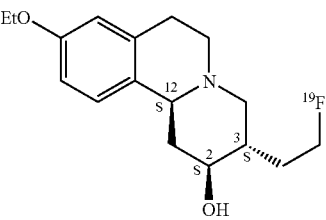 |
| 8c | 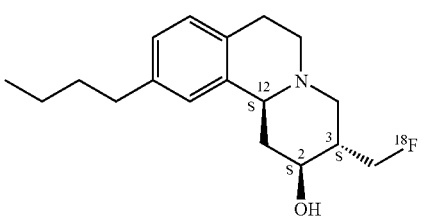<br>88 mole % | 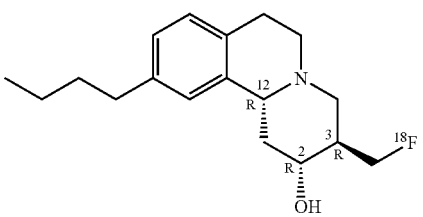 | and is comprised of at least 95 mole percent (mole %) of an enantiomer having the R configuration at ring position-12.

In an alternate embodiment, the present invention provides an alpha-fluoroalkyl dihydrotetrabenazine compound represented by structure IV which is enantiomerically enriched and is comprised of at least 95 mole percent (mole %) of an enantiomer having the R configuration at ring position-3.

In one embodiment, the present invention provides an alpha-fluoroalkyl dihydrotetrabenazine compound having structure IV in which the fluorinated aliphatic radical at ring position-3 (—$R^1$) has a syn-configuration relative to the hydrogen at ring position-12. The principal component enantiomers of Entries 8a-8c of Table 8 illustrate alpha-fluoroalkyl dihydrotetrabenazine compounds in which the fluorinated aliphatic moiety at ring position-3 (—$R^1$) has a syn-configuration relative to the hydrogen at ring position-12.

In one embodiment, the present invention provides an enantiomerically enriched alpha-fluoroalkyl dihydrotetrabenazine compound comprising a principal component enantiomer having structure V (V)

wherein $R^1$ is a $C_1$-$C_{10}$ fluorinated aliphatic radical; $R^2$ is hydrogen or a $C_1$-$C_{10}$ aliphatic radical; and $R^3$ is hydrogen or a $C_1$-$C_{10}$ aliphatic radical.

Principal component enantiomers having structure V are illustrated in Table 9 below.

TABLE 9

Principal Component Enantiomers Having Structure V

| Entry | Structure |
|---|---|
| 9a | 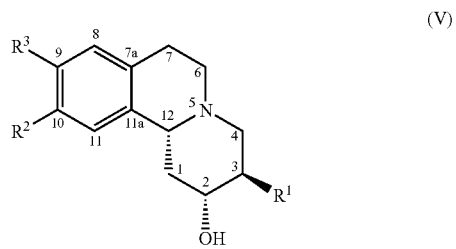 |
| 9b | 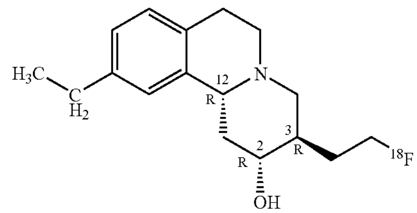 |
| 9c | 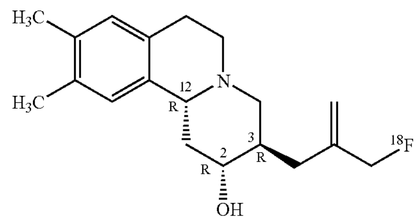 |

In one embodiment, the present invention provides an enantiomerically enriched alpha-fluoroalkyl dihydrotetrabenazine compound comprising at least 80 mole percent of an enantiomer having structure V, for example the composition comprising the compound of Entry 9a (Table 9) wherein the R, R, R enantiomer shown represents at least 80 mole percent relative to the amounts of all other alpha-fluoroalkyl dihydrotetrabenazine components in the composition.

In an alternate embodiment, the present invention provides an enantiomerically enriched alpha-fluoroalkyl dihydrotetrabenazine compound which is comprised of at least 95 mole % of an enantiomer having structure V, for example an alpha-fluoroalkyl dihydrotetrabenazine composition comprising the compound of Entry 9b (Table 9 wherein the R, R, R enantiomer shown represents at least 95 mole percent relative to the amounts of all other alpha-fluoroalkyl dihydrotetrabenazine components in the composition.

In one embodiment, the present invention provides an enantiomerically enriched alpha-fluoroalkyl dihydrotetrabenazine compound comprising a principal component enantiomer having structure V wherein $R^1$ is a $C_5$-$C_{10}$ fluorinated aliphatic radical; and $R^2$ and $R^3$ are methoxy groups and which are illustrated in Table 10 below.

TABLE 10

Principal Component Enantiomers Having Structure V Wherein $R^1$ Is A $C_5$-$C_{10}$ Fluorinated Aliphatic Radical And $R^2$ And $R^3$ Are Methoxy Groups

| Entry | Structure |
|---|---|
| 10a | 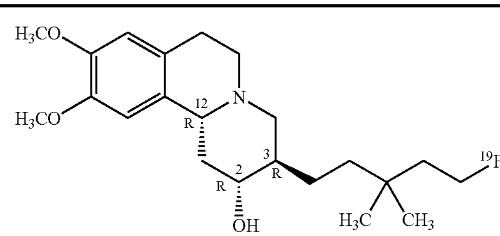 |

TABLE 10-continued

Principal Component Enantiomers Having Structure V Wherein $R^1$ Is A $C_5$-$C_{10}$ Fluorinated Aliphatic Radical And $R^2$ And $R^3$ Are Methoxy Groups

| Entry | Structure |
|---|---|
| 10b | (structure with H$_3$CO groups, N-containing tricyclic core, OH at C2, and side chain —CH$_2$CH$_2$C(CH$_3$)$_2$CH$_2$CH$_2$—$^{18}$F at C3) |
| 10c | (structure with H$_3$CO groups, tricyclic core, OH at C2, and side chain —(CH$_2$)$_6$—S—CH$_2$CH$_2$—$^{19}$F at C3) |
| 10d | (structure with H$_3$CO groups, tricyclic core, OH at C2, and side chain —(CH$_2$)$_6$—S—CH$_2$CH$_2$—$^{18}$F at C3) |

In one embodiment, the present invention provides an enantiomerically enriched alpha-fluoroalkyl dihydrotetrabenazine compound comprising a principal component enantiomer having structure VI

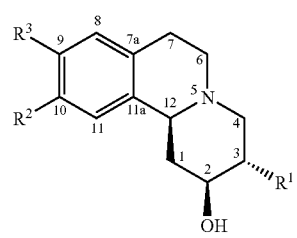

(VI)

wherein $R^1$ is a $C_1$-$C_{10}$ fluorinated aliphatic radical; $R^2$ is hydrogen or a $C_1$-$C_{10}$ aliphatic radical; and $R^3$ is hydrogen or a $C_1$-$C_{10}$ aliphatic radical.

Principal component enantiomers having structure VI are illustrated in Table 11 below.

TABLE 11

Principal Component Enantiomers Having Structure VI

| Entry | Structure |
|---|---|
| 11a | (structure with H$_3$CO and Si(Me)$_2$t-Bu—O substituents on aromatic ring, S-configured tricyclic core, OH at C2, and —CH$_2$CH$_2$CH$_2$—$^{19}$F side chain at C3) |
| 11b | (structure with H$_3$C, H$_3$C substituents on aromatic ring, S-configured tricyclic core, OH at C2, and —CH$_2$—C(=CH$_2$)—CH$_2$—$^{18}$F side chain at C3) |
| 11c | (structure with H$_3$C, H$_3$C substituents on aromatic ring, S-configured tricyclic core, OH at C2, and —CH$_2$CH$_2$—O—CH$_2$—S—CH$_2$CH$_2$—$^{18}$F side chain at C3) |

In one embodiment, the present invention provides an enantiomerically enriched alpha-fluoroalkyl dihydrotetrabenazine compound comprising at least 80 mole percent of an enantiomer having structure VI, for example an alpha-fluoroalkyl dihydrotetrabenazine composition comprising the compound of Entry 11a (Table 11) wherein the S, S, S enantiomer shown represents at least 80 mole percent relative to the amounts of all other alpha-fluoroalkyl dihydrotetrabenazine components in the composition. In another embodiment, the present invention provides an enantiomerically enriched alpha-fluoroalkyl dihydrotetrabenazine compound comprising at least 95 mole percent of an enantiomer having structure VI, for example an alpha-fluoroalkyl dihydrotetrabenazine composition comprising the compound of Entry 11b (Table 11) wherein the S, S, S enantiomer shown represents at least 95 mole percent relative to the amounts of all other alpha-fluoroalkyl dihydrotetrabenazine components in the composition.

In another embodiment, the present invention provides an enantiomerically enriched alpha-fluoroalkyl dihydrotetrabenazine compound comprising a principal component enantiomer having structure VI wherein $R^1$ is a $C_5$-$C_{10}$ fluorinated aliphatic radical; and $R^2$ and $R^3$ are methoxy groups, and which are illustrated in Table 12 below.

TABLE 12

Principal Component Enantiomers Having Structure VI Wherein $R^1$ Is A $C_5$-$C_{10}$ Fluorinated Aliphatic Radical; And $R^2$ And $R^3$ Are Methoxy Groups

| Entry | Structure |
|---|---|
| 12a | 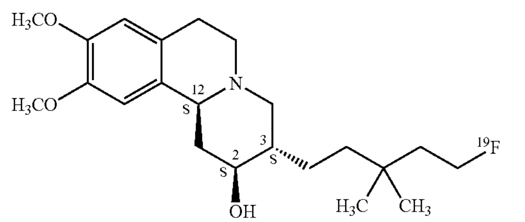 |
| 12b | 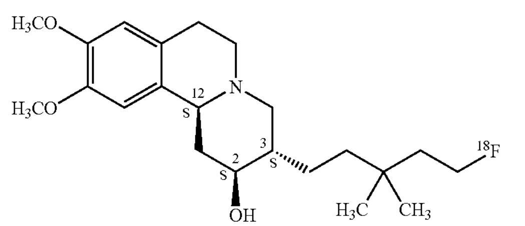 |
| 12c | 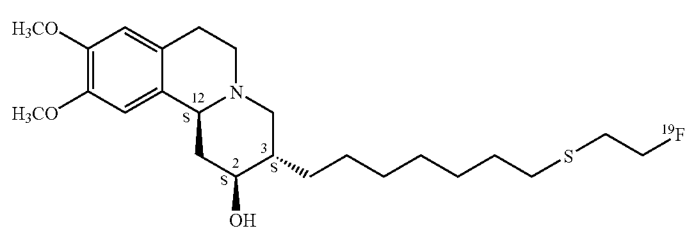 |
| 12d | 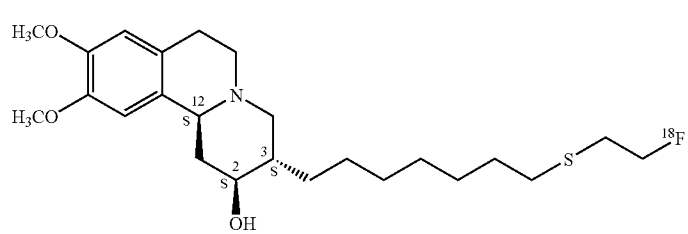 |

The alpha-fluoroalkyl tetrabenazine and dihydrotetrabenazine compounds provided by the present invention are at times herein referred to collectively as "alpha-fluoroalkyl compounds". As will be clear to one of ordinary skill in the art, the term "alpha-fluoroalkyl" refers to the group $R^1$ of structures I-VI which represents a $C_1$-$C_{10}$ aliphatic radical and is not restricted to the ordinary meaning of the term "alkyl". Thus although the term alpha-fluoroalkyl tetrabenazine is used extensively herein for convenience and means a tetrabenazine compound comprising a $C_1$-$C_{10}$ fluorinated aliphatic radical at ring position-3. Similarly, alpha-fluoroalkyl dihydrotetrabenazine refers to a dihydrotetrabenazine compound comprising a $C_1$-$C_{10}$ fluorinated aliphatic radical at ring position-3.

As noted, the alpha-fluoroalkyl tetrabenazine and dihydrotetrabenazine compounds I, II, III, IV, V, and VI provided by the present invention may comprise a fluorine-18 atom in the fluorinated aliphatic moiety —$R^1$. In various embodiments such alpha-fluoroalkyl compounds comprising a fluorine-18 atom are useful as PET imaging agents. Thus, in one embodiment, the present invention provides a PET imaging agent comprising an alpha-fluoroalkyl tetrabenazine compound having structure I

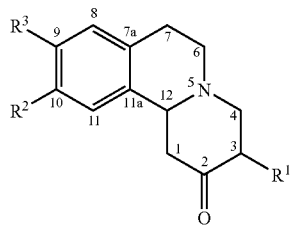

(I)

wherein $R^1$ is a $C_1$-$C_{10}$ fluorinated aliphatic radical comprising at least one fluorine-18 atom; $R^2$ is hydrogen or a $C_1$-$C_{10}$ aliphatic radical; and $R^3$ is hydrogen or a $C_1$-$C_{10}$ aliphatic radical.

In another embodiment, the present invention provides a PET imaging agent comprising an enantiomerically enriched alpha-fluoroalkyl tetrabenazine compound comprising a principal component enantiomer having structure II

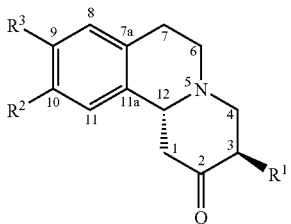

(II)

wherein $R^1$ is a $C_1$-$C_{10}$ fluorinated aliphatic radical comprising at least one fluorine-18 atom; $R^2$ is hydrogen or a $C_1$-$C_{10}$ aliphatic radical; and $R^3$ is hydrogen or a $C_1$-$C_{10}$ aliphatic radical.

In yet another embodiment, the present invention provides a PET imaging agent comprising an enantiomerically enriched alpha-fluoroalkyl tetrabenazine compound comprising a principal component enantiomer having structure III

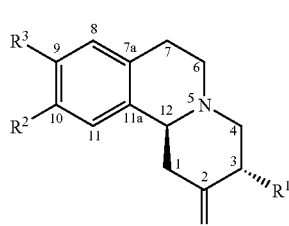

(III)

wherein $R^1$ is a $C_1$-$C_{10}$ fluorinated aliphatic radical comprising at least one fluorine-18 atom; $R^2$ is hydrogen or a $C_1$-$C_{10}$ aliphatic radical; and $R^3$ is hydrogen or a $C_1$-$C_{10}$ aliphatic radical.

In another embodiment, the present invention provides a PET imaging agent comprising an enantiomerically enriched alpha-fluoroalkyl tetrabenazine compound having structure I, wherein $R^1$ is a $C_5$-$C_{10}$ fluoraliphatic radical comprising at least one fluorine-18 atom, and $R^2$ and $R^3$ are methoxy groups.

In one embodiment, the present invention provides a PET imaging agent comprising an alpha-fluoroalkyl dihydrotetrabenazine compound having structure IV

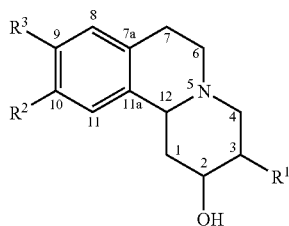

(IV)

wherein $R^1$ is a $C_1$-$C_{10}$ fluorinated aliphatic radical comprising at least one fluorine-18 atom; $R^2$ is hydrogen or a $C_1$-$C_{10}$ aliphatic radical; and $R^3$ is hydrogen or a $C_1$-$C_{10}$ aliphatic radical.

In another embodiment, the present invention provides a PET imaging agent comprising an enantiomerically enriched alpha-fluoroalkyl dihydrotetrabenazine compound comprising a principal component enantiomer having structure V

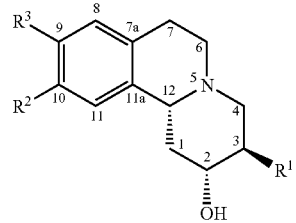

(V)

wherein $R^1$ is a $C_1$-$C_{10}$ fluorinated aliphatic radical comprising at least one fluorine-18 atom; $R^2$ is hydrogen or a $C_1$-$C_{10}$ aliphatic radical; and $R^3$ is hydrogen or a $C_1$-$C_{10}$ aliphatic radical.

In yet another embodiment, the present invention provides a PET imaging agent comprising an enantiomerically enriched alpha-fluoroalkyl dihydrotetrabenazine compound comprising a principal component enantiomer having structure VI

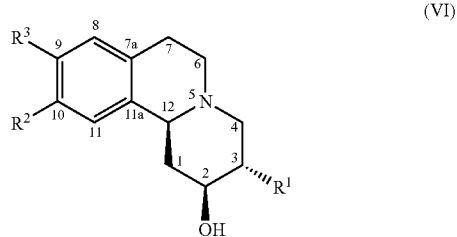

wherein $R^1$ is a $C_1$-$C_{10}$ fluorinated aliphatic radical comprising at least one fluorine-18 atom; $R^2$ is hydrogen or a $C_1$-$C_{10}$ aliphatic radical; and $R^3$ is hydrogen or a $C_1$-$C_{10}$ aliphatic radical.

In another embodiment, the present invention provides a PET imaging agent comprising an enantiomerically enriched alpha-fluoroalkyl dihydrotetrabenazine compound having structure IV, wherein $R^1$ is a $C_5$-$C_{10}$ fluoraliphatic radical comprising at least one fluorine-18 atom; and $R^2$ and $R^3$ are methoxy groups.

The term "PET imaging agent" as used herein refers to a composition comprising a fluorine-18 labeled alpha-fluoroalkyl tetrabenazine or dihydrotetrabenazine compound which may be administered to a patient in order to perform a PET scan. Typically, the imaging agent is presented to the patient in the form of an aqueous formulation containing a sufficient amount of fluorine-18 labeled alpha-fluoroalkyl tetrabenazine or dihydrotetrabenazine compound to conduct the PET scan. Typically, the amount of fluorine-18 labeled alpha-fluoroalkyl tetrabenazine or dihydrotetrabenazine compound presented to a patient corresponds to a weight of the fluorine-18 labeled alpha-fluoroalkyl compound on the order of nanograms. In reference to the relative amounts of non-radioactive fluorine-19 containing alpha-fluoroalkyl compound present in the PET imaging agent presented to a patient, the PET imaging agent typically has a specific activity in a range from about 1 to about 99 percent. In one embodiment, the PET imaging agent has a specific activity in a range from about 10 to about 95 percent. In another embodiment, the PET imaging agent has a specific activity in a range from about 20 to about 90 percent.

The aqueous formulation containing the fluorine-18 alpha-fluoroalkyl tetrabenazine or dihydrotetrabenazine compound is typically administered intravenously and may contain various agents which promote the dispersal of the PET imaging agent in water. In one embodiment, the PET imagining agent may be administered to a patient in an aqueous formulation comprising ethanol and the fluorine-18 labeled alpha-fluoroalkyl compound. In an alternate embodiment, the PET imagining agent may be administered to a patient as an aqueous formulation comprising dextrose and the fluorine-18 labeled alpha-fluoroalkyl compound. In yet another embodiment, the PET imagining agent may be administered to a patient as an aqueous formulation comprising saline and the fluorine-18 labeled alpha-fluoroalkyl compound.

In one embodiment, the present invention provides a PET imaging agent comprising both an alpha-fluoroalkyl tetrabenazine compound I and an alpha-fluoroalkyl dihydrotetrabenazine compound IV.

In addition to being useful as PET imaging agents and as probes for determining the suitability of a given alpha-fluoroalkyl compound for use as a PET imaging agent, the alpha-fluoroalkyl compounds provided by the present invention are believed to possess therapeutic utility in the treatment of diseases such as schizophrenia and Huntington's disease. Thus, in one embodiment, the present invention provides an alpha-fluoroalkyl tetrabenazine compound having structure I which is useful in treating a pathological condition in a patient. In an alternate embodiment, the present invention provides an alpha-fluoroalkyl dihydrotetrabenazine compound having structure IV which is useful in treating a pathological condition in a patient. In various other embodiments, the present invention provides enantiomerically enriched alpha-fluoroalkyl tetrabenazine and dihydrotetrabenazine compounds II, III, V, and VI (and mixtures thereof) which are useful in treating a pathological condition in a patient. Typically the amount of the alpha-fluoroalkyl compound administered to a patient in a given dose is on the order of milligrams.

Those skilled in the art will appreciate that alpha-fluoroalkyl compounds such as alpha-fluoroalkyl compounds falling within the scope of generic structure I, or generic structure IV may under a variety of conditions form salts which are useful as PET imaging agents, probes for the discovery and development of imaging agents, and/or as therapeutic agents. Thus, the present invention provides a host of novel and useful alpha-fluoroalkyl compounds and their salts. For example, in one particular embodiment, the present invention provides the hydrochloride salts of the novel alpha-fluoroalkyl compounds, for example the hydrochloride salt of the compound of Entry 6a of Table 6.

The alpha-fluoroalkyl tetrabenazine and dihydrotetrabenazine compounds of the present invention may be prepared by a variety of methods including those provided in the experimental section of this disclosure. In one embodiment, the alpha-fluoroalkyl tetrabenazine compound is prepared by reaction of nucleophilic fluoride ion or an electrophilic fluorinating agent with a fluorophilic tetrabenazine compound having structure VII

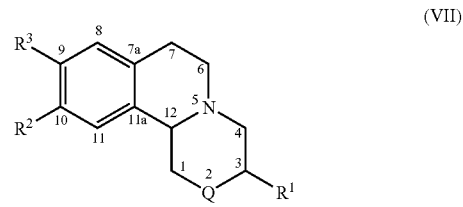

wherein Q is a carbonyl group, a protected carbonyl group, a hydroxy methine group, or a protected hydroxy methine group; $R^1$ is a $C_1$-$C_{20}$ aliphatic, $C_2$-$C_{20}$ cycloaliphatic, or $C_2$-$C_{20}$ aromatic radical comprising at least one functional group susceptible to reaction with nucleophilic fluoride ion or an electrophilic fluorinating agent; $R^2$ is hydrogen or a $C_1$-$C_{10}$ aliphatic radical; and $R^3$ is hydrogen or a $C_1$-$C_{10}$ aliphatic radical.

Thus in one embodiment, the present invention provides a fluorophilic tetrabenazine compound having structure VII. Fluorophilic tetrabenazine compounds having structure VII are illustrated in Table 13 below.

TABLE 13

Examples of Fluorophilic Tetrabenazine Compounds Having Structure VII

| Entry | Q | R¹ | R² | R³ | Ring Position Stereochemistry RP-3 | RP-12 |
|---|---|---|---|---|---|---|
| 13a | [-]CHOTHP | 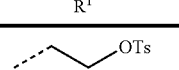 | $CH_3$ | $CH_3$ | R/S | R/S |
| 13b | [-]CHOH | 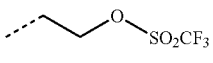 | $CH_3$ | $CH_3$ | R | R |
| 13c | C=O | 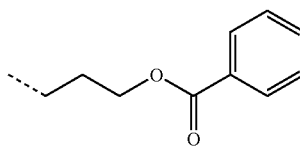 | $CH_3O$ | $CH_3O$ | R/S | R/S |
| 13d | [-]CHOAc | 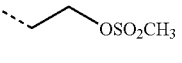 | $CH_3O$ | $CH_3O$ | R | R |
| 13e | C=O | 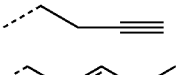 | EtO | $CH_3O$ | S | S |
| 13f | [-]CHOH | 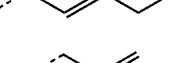 | EtO | EtO | S | S |
| 13g | [-]CHOCH$_2$SCH$_3$ | 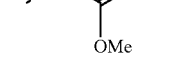 | $CH_3CH_2$ | $CH_3CH_2$ | R/S | R/S |
| 13h |  | 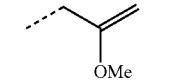 | $CH_3O$ | $CH_3O$ | R | R |
| 13i |  | 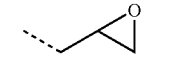 | $CH_3O$ | $CH_2CH_3$ | R/S | R/S |
| 13j |  | 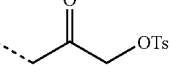 | $CH_3O$ | H | R/S | R |
| 13k |  | 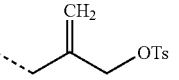 | $CH_3O$ | $CH_3O$ | R | R |
| 13l | 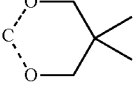 |  | $CH_3O$ | $CH_3O$ | R | R |

As provided for in generic structure VII, the fluorophilic tetrabenazine compounds of the present invention include compounds which are formally tetrabenazine compounds (i.e., Q is a carbonyl group, for example Entries 13c and 13e of Table 13); compounds which are formally dihydrotetrabenazine compounds (i.e., Q is a hydroxy methine group); "protected" tetrabenazine compounds (i.e., Q is a protected carbonyl group, for example Q is ethylene ketal group as found in tetrabenazine ketal tosylate 33 of Example 4 herein); or "protected" dihydrotetrabenazine compounds (i.e., Q is a protected hydroxy methine group, for example Q is a CHOTHP group as in Entry 13a of Table 13 and in tosylate 34 of Example 5 herein). Thus, the term "protected carbonyl group" refers to a carbonyl group equivalent, usually a carbonyl group which has been transformed into a functional group such as a ketal, thioketal, or dithioketal group; and the term "protected hydroxy methine group" refers to a hydroxy methine group equivalent, usually a hydroxy methine group which has been transformed into a functional group such as a tetrahydropyranyl (THP) ether group, a methoxymethyl ether group (MOM group), a methoxyethoxyether group (MEM group), a methylthiomethyl ether group, a benzyl ether group, a p-methoxybenzyl ether group, a pivaloyl ester group (OPiv), or an actetyl ester group (OAc). Protection agents which may be used to transform a carbonyl group or a hydroxy methine group into a protected carbonyl group or a protected hydroxy methine group are well known in the art, for example protection agents detailed in Protecting Groups In Organic Synthesis by James R. Hanson (Blackwell Science, 1999) and Greene's Protective Groups in Organic Synthesis (Wiley-Interscience, 2006).

As noted, in one embodiment, the present invention provides a fluorophilic compound having structure VII, wherein $R^1$ is a $C_1$-$C_{20}$ aliphatic radical, a $C_2$-$C_{20}$ cycloaliphatic radical, or a $C_2$-$C_{20}$ aromatic radical comprising at least one functional group susceptible to reaction with nucleophilic fluoride ion. In one embodiment, the functional group susceptible to reaction with nucleophilic fluoride ion is an aromatic sulfonate ester (e.g. tosylate, benzenesulfonate, naphthalenesulfonate). In an alternate embodiment, the functional group susceptible to reaction with nucleophilic fluoride ion is an aliphatic sulfonate ester (e.g. methane sulfonate, trifluoromethane sulfonate). In one embodiment, the functional group susceptible to reaction with nucleophilic fluoride ion is selected from the group consisting of tosylate, mesylate, and trifluoromethane sulfonate groups.

In one embodiment, the present invention provides a fluorophilic compound having structure VII wherein the group $R^1$ comprises at least one tosylate group susceptible to reaction with nucleophilic fluoride ion. See for example the Entries 13a, 13j and 13k of Table 13. As defined herein, the tosylate group is an aromatic radical and the group $R^1$ comprising the tosylate group is also an aromatic radical. In the compound shown in Entry 13a for example, the group $R^1$ comprising the tosylate group is a $C_9$ aromatic radical which upon displacement with fluoride ion becomes a $C_2$ fluorinated aliphatic radical.

In an alternate embodiment, the present invention provides a fluorophilic compound having structure VII wherein the group $R^1$ comprises at least one mesylate group susceptible to reaction with nucleophilic fluoride ion. As defined herein, the mesylate group is an aliphatic radical and the group $R^1$ comprising the mesylate group may be an aliphatic, a cycloaliphatic or an aromatic radical depending on the overall structure of the group $R^1$. For example, in a fluorophilic compound having structure VII in which $R^1$ comprises both a mesylate group and an epoxy group, the group $R^1$ is a cycloaliphatic radical. Alternatively, in a fluorophilic compound having structure VII in which $R^1$ comprises both a mesylate group and a tosylate group, the group $R^1$ is an aromatic radical. It is helpful to bear in mind that the definitions of aliphatic, cycloaliphatic and aromatic radicals provided in this disclosure establish a hierarchy in which aliphatic radicals (non-cyclic arrays of atom(s)) must be free of cycloaliphatic groups (a cyclic array of atoms which is not aromatic) and aromatic groups (a cyclic array of atoms which is aromatic), cycloaliphatic radicals must be free of aromatic groups, and aromatic radicals must simply comprise an aromatic group.

In an alternate embodiment, the present invention provides a fluorophilic compound having structure VII wherein the group $R^1$ comprises at least one trifluoromethane sulfonate (triflate) group susceptible to reaction with nucleophilic fluoride ion. See for example Entry 13b of Table 13.

In an alternate embodiment, the present invention provides a fluorophilic compound having structure VII wherein the group $R^1$ comprises at least one p-nitrobenzoate group susceptible to reaction with nucleophilic fluoride ion. See for example Entry 13c of Table 13.

In an alternate embodiment, the present invention provides a fluorophilic compound having structure VII wherein the group $R^1$ comprises at least one methane sulfonate group susceptible to reaction with nucleophilic fluoride ion. See for example Entry 13d of Table 13.

In an alternate embodiment, the present invention provides a fluorophilic compound having structure VII wherein the group $R^1$ comprises at least one epoxy group susceptible to reaction with nucleophilic fluoride ion. See for example Entry 13i of Table 13.

In yet another embodiment, the present invention provides a fluorophilic compound having structure VII wherein the group $R^1$ comprises at least one cyclic sulfate group susceptible to reaction with nucleophilic fluoride ion. See for example Entry 13l of Table 13.

In one embodiment, the present invention provides a fluorophilic compound having structure VII, wherein $R^1$ is a $C_2$-$C_{20}$ aliphatic radical comprising at least one functional group susceptible to reaction with an electrophilic fluorinating agent, for example fluorine gas, perchloryl fluoride, mercuric fluoride, and phenyl selenenyl fluoride.

Thus in one embodiment, the functional group susceptible to reaction with an electrophilic fluorinating agent is selected from the group consisting of carbon-carbon double bonds and carbon-carbon triple bonds. Entries 13e, 13f, 13g, 13h and 13k of Table 13 illustrate compounds falling within the scope of generic structure VII which are susceptible to reaction with an electrophilic fluorinating agent. Attention is called to Entry 13k wherein the group $R^1$ comprises functional groups susceptible to reaction with an electrophilic fluorinating agent (double bond) and to reaction with nucleophilic fluoride ion (tosylate group). Entry 13k of Table 13 also features a thioketal carbonyl protecting group. As used herein a thioketal protecting group comprises both an oxygen and a sulfur atom bonded to the "carbonyl carbon" and is distinguished from a dithioketal which comprises two sulfur atoms attached to the "carbonyl carbon", for example as in Entry 13j of Table 13.

Fluorophilic tetrabenazine compounds VII may be prepared in enantiomerically enriched or racemic forms. For example, a fluorophilic tetrabenazine compound VII may be enriched in the R,R-enantiomer shown in Entry 13h of Table 13. Alternatively, a fluorophilic tetrabenazine compound may be enriched in an enantiomer having absolute stereochemistry opposite that of Entry 13d of Table 13, for example the S,S-enantiomer of Entry 13e.

Thus, in one embodiment, the present invention provides an enantiomerically enriched fluorophilic compound comprising a principal component enantiomer having structure VIII

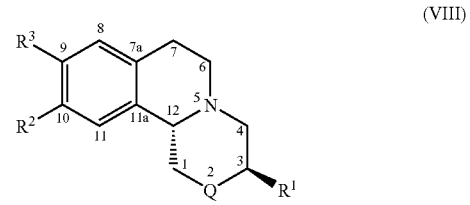

(VIII)

wherein Q is a carbonyl group, a protected carbonyl group, a hydroxy methine group, or a protected hydroxy methine group; $R^1$ is a $C_1$-$C_{20}$ aliphatic, $C_2$-$C_{20}$ cycloaliphatic, or $C_2$-$C_{20}$ aromatic radical comprising at least one functional group susceptible to reaction with nucleophilic fluoride ion or an electrophilic fluorinating agent; $R^2$ is hydrogen or a $C_1$-$C_{10}$ aliphatic radical; and $R^3$ is hydrogen or a $C_1$-$C_{10}$ aliphatic radical. Principal component enantiomers VIII are illustrated by Entries 13b, 13d, 13h, and 13k of Table 13.

In an alternate embodiment, the present invention provides an enantiomerically enriched fluorophilic compound comprising a principal component enantiomer having structure IX

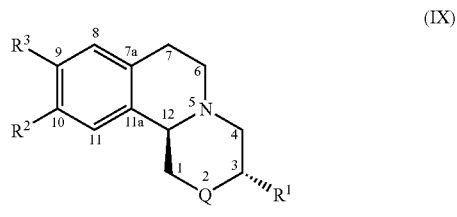

(IX)

wherein Q is a carbonyl group, a protected carbonyl group, a hydroxy methine group, or a protected hydroxy methine group; $R^1$ is a $C_1$-$C_{20}$ aliphatic, $C_2$-$C_{20}$ cycloaliphatic, or $C_2$-$C_{20}$ aromatic radical comprising at least one functional group susceptible to reaction with nucleophilic fluoride ion or an electrophilic fluorinating agent; $R^2$ is hydrogen or a $C_1$-$C_{10}$ aliphatic radical; and $R^3$ is hydrogen or a $C_1$-$C_{10}$ aliphatic radical. Principal component enantiomers IX are illustrated by Entries 13e and 13f of Table 13.

Co-pending U.S. patent application Ser. No. 11/760,359 and Ser. No. 11/760,372 filed Jun. 8, 2007 disclose methods for the preparation of racemic and enantiomerically enriched tetrabenazine compositions which may be used in the preparation of compounds of the present invention. In addition, the Examples Section of the present disclosure provides detailed experimental descriptions of the preparation and characterization of fluorophilic tetrabenazine compounds VII and their conversion to alpha-fluoroalkyl tetrabenazine compounds I and alpha-fluoroalkyl dihydrotetrabenazine compounds IV.

In general, fluorophilic tetrabenazine compounds VII can be prepared by reacting a nucleophilic alkenyl species with an aldehyde compound having structure X

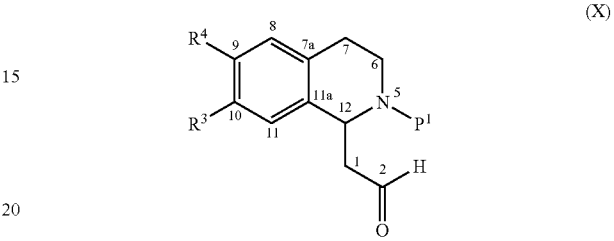

(X)

wherein $R^3$ is hydrogen or a $C_1$-$C_{20}$ aliphatic radical; and $R^4$ is hydrogen or a $C_1$-$C_{20}$ aliphatic radical; and $P^1$ is a protecting group, to provide an allylic alcohol (See Methods 4, 5, and 6 of the Examples section), which is then oxidized to provide an enone designated the "first intermediate" (See Methods 7, 8, and 9 of the Examples section), the protecting group $P^1$ of which is then removed and the resultant deprotected first intermediate undergoes an amino cyclization reaction to afford the corresponding TBZ compound.

Representative aldehyde compounds encompassed by generic formula X are given in Table 14.

TABLE 14

Representative Aldehyde Compounds Encompassed By Formula X

| Entry | Compound Type | Ring Position* Stereochemistry | Structure |
|---|---|---|---|
| 14a | Single "R" enantiomer, "Boc" protecting group $P^1$ | RP-12 "R" | 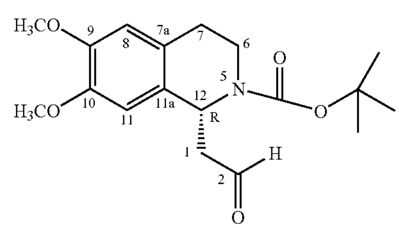 |
| 14b | Single "S" enantiomer, "Boc" protecting group $P^1$ | RP-12 "S" | 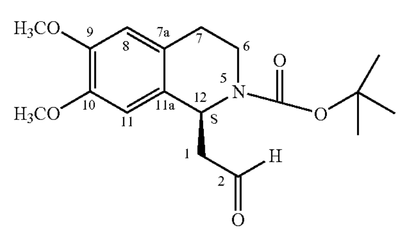 |

TABLE 14-continued

Representative Aldehyde Compounds Encompassed By Formula X

| Entry | Compound Type | Ring Position* Stereo-chemistry | Structure |
|---|---|---|---|
| 14c | Enantiomerically enriched mixture of "R" and "S" enantiomers; "alloc" protecting group $P^1$ | RP-12 "R/S" | |
| 14d | Racemic mixture of "R" and "S" enantiomers; "Fmoc" protecting group $P^1$ | RP-12 "R/S" | 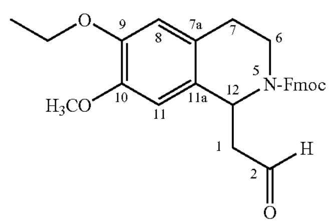 |
| 14e | Racemic mixture of "R" and "S" enantiomers; "Cbz" protecting group $P^1$ | RP-12 "R/S" | 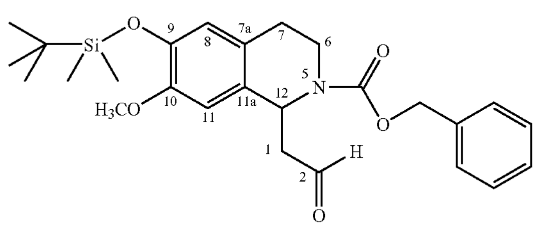 |
| 14f | Racemic mixture of "R" and "S" enantiomers; "Teoc" protecting group $P^1$ | RP-12 "R/S" | 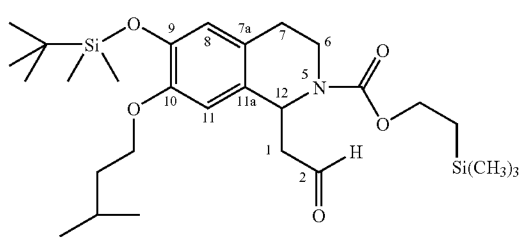 |
| 14g | Single "R" enantiomer, "Boc" protecting group $P^1$ | RP-12 "R" | 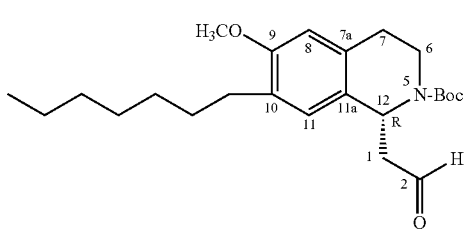 |

The preparation of the aldehyde compound featured in Entry 14a of Table 14 is described in the Examples section of this disclosure (Methods 1-3). In general, the class of aldehyde compounds represented by structure X may be prepared by art recognized methods, for example using the methodology depicted in Scheme 1. Those skilled in the art will appreciate that as depicted in Scheme 1 the protecting group $P^1$ represents a "Boc" protecting group.

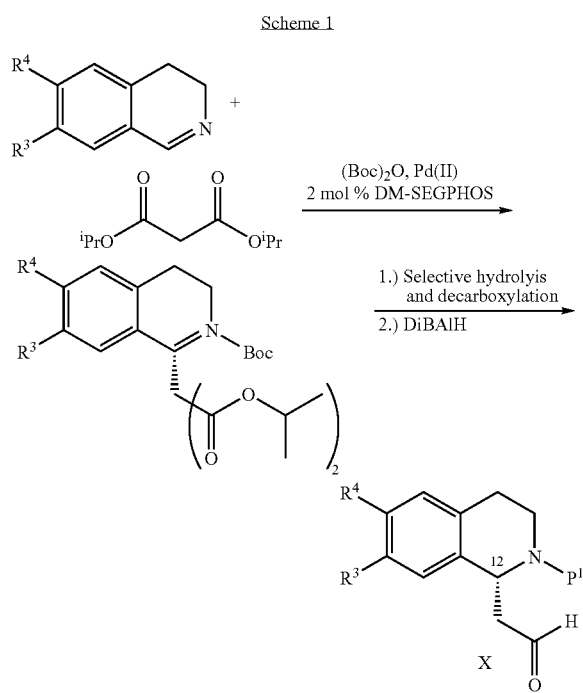

Thus, aldehyde compounds X may be prepared from intermediates prepared using methodology described by Sasamoto et al. (Journal of the American Chemical Society 128, 14010-14011, 2006). Sasamoto et al. disclose the preparation of enantiomerically enriched tetrahydroquinoline malonate compounds which may be converted as shown in the present disclosure to aldehyde compound X by selective hydrolysis of one of the ester moieties of the tetrahydroquinoline malonate and decarboxylation followed by reduction of the resultant tetrahydroisoquinoline monoester to aldehyde compound X as depicted in Scheme 1.

One of ordinary skill in the art will appreciate that the 2 mole percent DM-SEGPHOS shown in Scheme 1 represents a chiral catalyst responsible for the enantiomeric enrichment of the product aldehyde X, and further that the use of DM-SEGPHOS of opposite chirality as the chiral catalyst will afford a product aldehyde X enantiomerically enriched in the "S" enantiomer (aldehyde compound X having the S configuration at ring position-12 (See for example Entry 14b of Table 14). Suitable chiral catalysts include those disclosed by Sasamoto et al. (Journal of the American Chemical Society 128, 14010-14011, 2006), for example (S)-Binap, (R)-Binap, (S)-DM-Binap, (R)-DM-Binap, (S)-DM-SEGPHOS, and (R)-DM-SEGPHOS. Typically use of a catalyst consisting of a ligand possessing a single, for example "S", configuration produces stereochemically enriched malonate adducts of the opposite "R" configuration and vice versa.

In addition to the use of a chiral catalyst to generate aldehyde compounds X enriched in a single configuration at ring position-12, there are available a wide variety of methods for the separation of racemic aldehyde X into its constituent enantiomers. For example, racemic aldehyde compound X may be separated into its constituent enantiomers by high performance liquid chromatography (hplc) on a chiral hplc column.

Other methods for producing enantiomerically enriched compositions provided by the present invention include conversion of a racemic alpha-fluoroalkyl compound having structure I compound into an adduct comprising a mixture of diastereomers which are then separated by fractional crystallization. For example, a racemic alpha-fluoroalkyl compound having structure I may be reacted with (–)-tartaric acid to form an adduct (ammonium tartarate salt) of the racemic alpha-fluoroalkyl compound, said adduct comprising a mixture of diastereomeric ammonium tartarate salts which are then separated by fractional crystallization.

EXAMPLES

The following examples are intended only to illustrate methods and embodiments in accordance with the invention, and as such should not be construed as imposing limitations upon the claims.

Methods for Preparing TBZ and DTBZ Starting Materials

Method 1 Preparation of Protected Diester 2

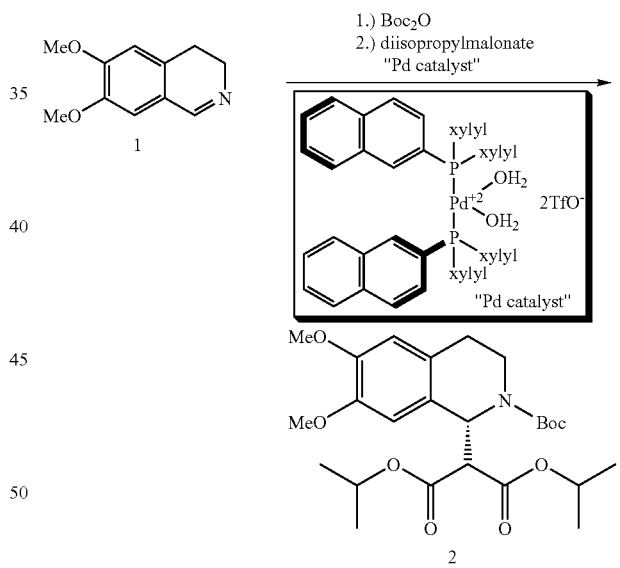

The dihydroisoquinoline 1 (1.0 eq.) and Boc anhydride (1.5 eq.) were dissolved in $CH_2Cl_2$ at room temperature to provide a 1.5 M solution with respect to the dihydroisoquinoline. The mixture was allowed to stir for 30 min. Following the allotted time, the reaction mixture was cooled to 0° C. and then diisopropylmalonate (1.5 eq.) followed by a pre-chilled solution of the Pd catalyst (0.008 eq.) in dichloromethane were added successively to the reaction mixture to provide a final reaction concentration of 0.84 M with respect to the starting dihydroisoquinoline. The reaction mixture was allowed to continue stirring at ~2.5° C. for 15 h. Following this time EtOAc and brine were added to the reaction mixture. The aqueous layer was extracted with three portions of EtOAc and the combined organic layers were dried (Na$_2$SO$_4$), filtered, and concentrated under reduced pressure to provide the crude product. The crude material was dissolved in a minimal amount of dichloromethane and purified by flash chromatography on SiO$_2$ (15-30% EtOAc-hexanes, elution was observed at 285 nm and 228 nm). The product 2 was a colorless solid that existed as a mixture of rotamers in solution at room temperature 94%: [α]$^{26}_D$ −69.0 (c 0.21, CHCl$_3$); $^1$H NMR (CDCl$_3$) δ 0.81-1.02 (m, 6H), 1.06-1.17 (m, 6H), 1.23-1.38 (m, 9H), 2.51-2.63 (m, 1H), 2.64-2.77 (m, 1H), 3.20-3.29 (m, 0.6H), 3.32-3.41 (m, 0.4H), 3.51-3.58 (m, 1H), 3.62-3.70 (m, 6H), 3.70-3.76 (m, 0.4H), 3.91-4.01 (m, 0.6H), 4.65-4.82 (m, 1H), 4.83-4.98 (m, 1H), 5.71 (apparent d, J=5.7 Hz, 0.6H), 5.78 (apparent d, J=7.9 Hz, 0.4H), 6.42-6.49 (m, 1H), 6.77 (s, 0.6H), 6.81 (s, 0.4H); $^{13}$C NMR (CDCl$_3$) δ 21.02, 21.09, 21.18, 21.32, 27.24, 27.95, 28.02, 37.60, 39.34, 52.11, 52.83, 55.48, 55.52, 59.28, 60.08, 68.58, 68.76, 68.82, 79.46, 80.03, 110.09, 110.73, 111.13, 126.11, 126.18, 126.37, 127.07, 146.81, 146.87, 147.93, 153.86, 154.30, 166.29, 166.78, 166.94, 167.06.

Method 2 Selective Hydrolysis and Decarboxylation of Protected Diester 2

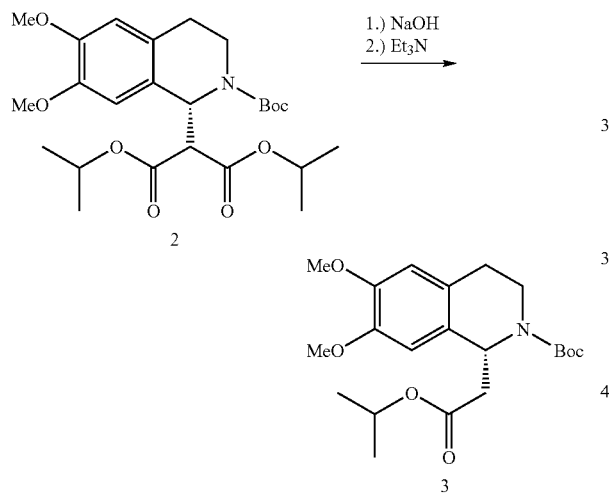

The starting material 2 was taken up in isopropanol to provide a 0.2 M solution of 2. To this solution was added 1M aqueous NaOH solution bringing the final concentration of the reaction mixture to 0.1M with respect to the malonate 2. The reaction mixture was heated to and maintained 70° C. for 22 min. (timing was started when the temperature of the reaction mixture temp exceeded 65° C.). Following the allotted time the reaction mixture was quickly cooled to 0° C. The reaction mixture carefully acidified with 2M aqueous HCl and extracted with three portions of dichloromethane. The combined organic extracts dried (Na$_2$SO$_4$), filtered and concentrated under reduced pressure. The isolated material was taken up in THF to provide a 0.1 M solution (based on the original quantity of 2 used in the reaction mixture) and triethylamine (1.0 eq) was added to the reaction mixture at room temperature. The reaction mixture was heated to its reflux temperature and maintained at this temperature for 90 min. The reaction mixture was concentrated under reduced pressure, dissolved in a minimal quantity of CH$_2$Cl$_2$ and was immediately purified by column chromatography on SiO$_2$ (15-40% EtOAc-hexanes; 40%, the eluant was monitored at 284 nm). The product 3 existed as a mixture of rotamers at room temperature and was a colorless foam 79%: [α]$^{26}_D$ −82 (c 0.24, CH$_2$Cl$_2$); $^1$H NMR (CDCl$_3$) δ 1.19-1.25 (m, 6H), 1.43-1.49 (m, 9H), 2.58-2.69 (m, 2H), 2.70-2.77 (m, 1H), 2.78-2.92 (m, 1H), 3.13-3.43 (m, 1H), 3.81-3.85 (m, 6H), 3.86-4.01 (m, 1H), 4.91-5.05 (m, 1H), 5.38-5.61 (m, 1H), 6.56-6.61 (m, 1H), 6.64-6.70 (s, 1H); $^{13}$C NMR (CDCl$_3$) δ 21.75, 21.90, 27.93, 28.08, 28.44, 37.53, 38.75, 42.22, 42.81, 51.11, 51.87, 55.92, 56.02, 68.08, 79.74, 80.21, 109.60, 109.99, 111.44, 111.54, 126.28, 126.48, 128.54, 128.76, 147.51, 147.97, 154.39, 154.51, 170.36, 170.59; LRMS-(ESI+) calcd for (C$_{21}$H$_{31}$NO$_6$+H) [M+H]$^+$ 394.22, found 394.16.

Method 3 Preparation of Aldehyde Compound 4

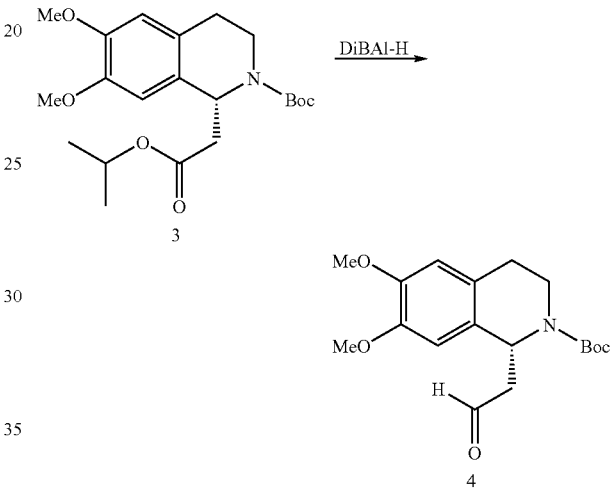

To a 0.12 M solution of the starting monoester (3, 1.0 eq.) in toluene at −78° C. was added a 1.5 M solution of DiBAl—H in hexanes (1.5 eq.) dropwise via a syringe pump. Following the addition the reaction mixture was stirred at −78° C. for 2 h. The reaction mixture was quenched by the addition of EtOAc and was then acidified with saturated aqueous citric acid solution. The reaction mixture was allowed to warm to room temperature and continue stirring for 30 min. The phases were separated, and the aqueous layer extracted with three portions of EtOAc. The combined organic extracts were washed with two portions of 2 M aqueous HCl solution, brine, dried (MgSO$_4$), filtered, and concentrated under reduced pressure. The crude product was subjected purification on SiO$_2$ (15-35% EtOAc-hexanes; Elution was observed at 285 nm and 228 nm). The isolated product aldehyde compound 4 was a colorless foam. The product existed as a 1:1 mixture of rotamers at room temperature 76%: [α]$^{26}_D$ −116 (c 0.26, CH$_2$Cl$_2$); $^1$H NMR (CDCl$_3$) δ 1.40 (s, 9H), 2.58 (apparent t, J=3.8 Hz, 0.5H), 2.61 (apparent t, J=3.5 Hz, 0.5H), 2.68-2.88 (m, 3H), 3.02-3.27 (m, 1H), 3.78 (apparent s, 6H), 3.87-3.99 (m, 0.5H), 4.08-4.23 (m, 0.5H), 5.37-5.68 (m, 1H), 6.55 (s, 1H), 6.58 (s, 1H), 9.78 (s, 1H); $^{13}$C NMR (CDCl$_3$) δ 20.90, 28.02, 28.27, 37.23, 38.65, 49.29, 49.93, 51.12, 55.83, 55.96, 80.13, 80.64, 109.42, 109.52, 111.52, 126.34, 126.51, 127.78, 127.82, 147.72, 147.97, 153.85, 154.62, 200.08, 200.33.

Method 4 Reaction of Aldehyde Compound 4 with Nucleophilic Alkenyl Species Derived from Alkenyl Iodide 5 with to Provide Allylic Alcohol 6

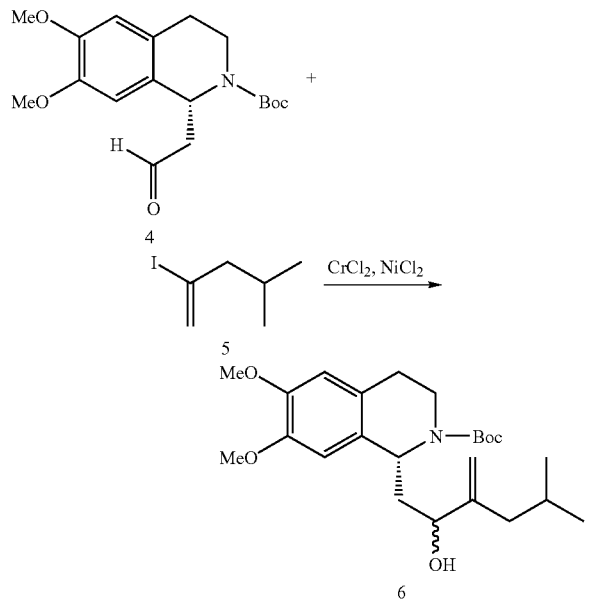

To a neat mixture of the alkenyl iodide 5 (1.0 eq) and the aldehyde compound 4 (1.0 eq.) at room temperature was added 2.65 eq. of chromium chloride doped with 0.5% NiCl$_2$ (w/w). The mixture was vortexed for about 2 min. to provide a homogeneous, green/grey paste and then stirred under nitrogen for an additional 10 min. after which time anhydrous DMF was added to bring the final reaction concentration to 0.36 M. The reaction mixture was deep green in color and was permitted to continue stirring at room temperature for 14 h. Following the allotted time, the reaction mixture was diluted with 1:1 EtOAc-hexanes and an aqueous 0.5 M EDTA solution (pH 9) was added and the entire mixture was allowed to stir for 1.5 h. The aqueous layer was extracted with three portions of EtOAc, dried (MgSO$_4$), filtered, and the filtrate was concentrated under reduced pressure to provide a green oil. The crude material was subjected to column chromatography on SiO$_2$ (35% EtOAc-hexanes; elution was observed at 285 nm and 228 nm). The product allylic alcohol 6 was a pale yellow oil isolated in 53% yield as a mixture of diastereomers which was taken on to the next step without additional characterization or analysis.

Method 5 Reaction of Aldehyde Compound 4 with Nucleophilic Alkenyl Species Derived from Alkenyl Iodide 7 with to Provide Allylic Alcohol 8

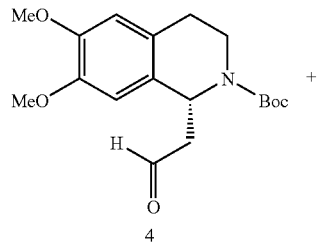

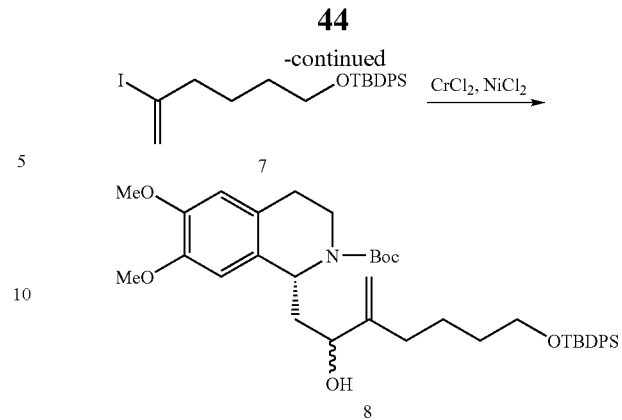

To a neat mixture of the alkenyl iodide 7 (1.0 eq) and the aldehyde compound 4 (1.25 eq.) at room temperature was added 2.5 eq. of chromium chloride doped with 0.5% NiCl$_2$ (w/w). The mixture was vortexed for about 2 min. to provide a homogeneous, green/grey paste and then stirred under nitrogen for an additional 10 min. after which time anhydrous DMF was added to bring the final reaction concentration to 0.32 M. The reaction mixture was deep green in color and was permitted to continue stirring at room temperature for 14 h. Following the allotted time, the reaction mixture was diluted with 1:1 EtOAc-hexanes and an aqueous 0.5 M EDTA solution (pH 9) was added and the entire mixture was allowed to stir for 1.5 h. The aqueous layer was extracted with three portions of EtOAc, dried (MgSO$_4$), filtered, and the filtrate was concentrated under reduced pressure to provide a green oil. The crude material was subjected to column chromatography on SiO$_2$ (20% EtOAc-hexanes to 35% EtOAc-hexanes; elution was observed at 285 nm and 228 nm). The product allylic alcohol 8 was a pale yellow oil isolated in 54% yield as a mixture of diastereomers which was taken on to the next step without additional characterization or analysis.

Method 6 Reaction of Aldehyde Compound 4 with Nucleophilic Alkenyl Species Derived from Alkenyl Iodide 9 with to Provide allylic Alcohol 10

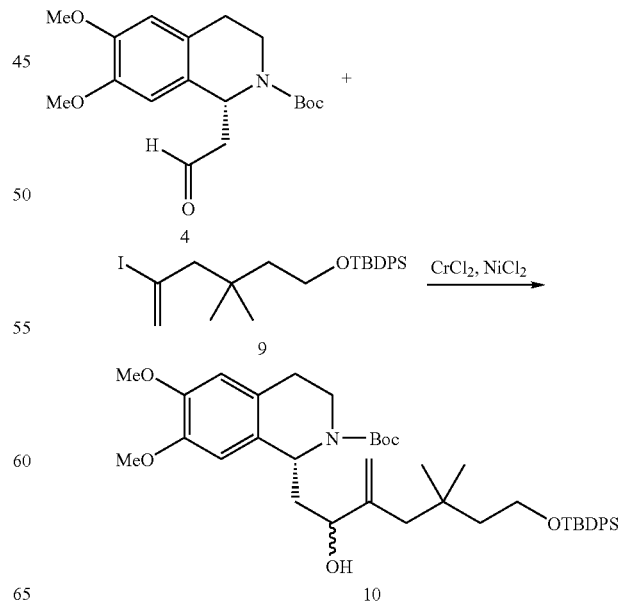

To a neat mixture of the alkenyl iodide 9 (1.5 eq) and the aldehyde 4 (1.0 eq.) at room temperature was added 2.5 eq. of chromium chloride doped with 0.5% $NiCl_2$ (w/w). The mixture was vortexed for about 2 min. to provide a homogeneous, green/grey paste and then stirred under nitrogen for an additional 10 min. after which time anhydrous DMF was added to bring the final reaction concentration to 0.36 M. The reaction mixture was deep green in color and was permitted to continue stirring at room temperature for 14 h. Following the allotted time, the reaction mixture was diluted with 1:1 EtOAc-hexanes and an aqueous 0.5 M EDTA solution (pH 9) was added and the entire mixture was allowed to stir for 1.5 h. The aqueous layer was extracted with three portions of EtOAc, dried ($MgSO_4$), filtered, and the filtrate was concentrated under reduced pressure to provide a green oil. The crude material was subjected to column chromatography on $SiO_2$ (40% EtOAc-hexanes; elution was observed at 285 nm and 228 nm) to afford the product allylic alcohol 10 as a pale yellow oil that existed as a 1:1 mixture of diastereomers (47%): $^1$H NMR ($CD_2Cl_2$) δ 0.94-1.00 (m, 6H), 1.13-1.16 (m, 9H), 1.54-1.57 (m, 9H), 1.67-1.74 (m, 2H), 1.79-1.86 (m, 0.5H), 1.87-1.94 (m, 1H), 1.96-2.05 (m, 0.5H), 2.09-2.24 (m, 2H), 2.66-2.77 (m, 1H), 2.85-2.99 (m, 1H), 3.16-3.22 (m, 0.5H), 3.36-3.44 (m, 0.5H), 3.80-3.92 (m, 8H), 4.01-4.08 (m, 0.5H), 4.12-4.17 (m, 0.5H), 4.30-4.38 (m, 0.5H), 4.66-4.77 (m, 0.5H), 4.86-4.96 (m, 1H), 5.23-5.30 (m, 0.5H), 5.34-5.39 (m, 1H), 5.39-5.43 (m, 0.5H), 6.68-6.72 (m, 1H), 6.73-6.77 (m, 0.5H), 6.77-6.81 (m, 0.5H), 7.43-7.52 (m, 6H), 7.75-7.82 (m, 4H); $^{13}$C NMR ($CD_2Cl_2$) δ 19.12, 26.83, 27.33, 27.45, 27.54, 27.59, 28.29, 28.41, 33.46, 33.48, 38.30, 39.45, 43.64, 43.82, 44.93, 45.05, 45.48, 45.95, 50.95, 52.25, 55.89, 55.99, 56.01, 61.14, 69.99, 73.06, 80.03, 80.49, 110.21, 110.56, 111.87, 112.00, 112.02, 112.39, 125.92, 126.32, 126.35, 127.77, 129.57, 129.69, 130.17, 134.15, 135.68, 147.85, 147.88, 147.99, 148.11, 148.71, 149.59, 149.61, 155.79, 156.39.

Method 7 Oxidation of Allylic Alcohol 6 to Provide First Intermediate 12

To a 0.1 M solution of allylic alcohol 6 (1.0 eq) in dichloromethane at 0° C. was added 1.1 eq. of the Dess-Martin reagent 11. The reaction mixture was allowed to stir, slowly warming to room temperature over 2.5 h. The reaction was quenched by the addition of saturated aqueous sodium bicarbonate solution and diluted with ethyl acetate. The organic and aqueous layers were partitioned and separated and the aqueous layer extracted with three additional portions of ethyl acetate. The combined organic extracts were washed with brine, dried ($MgSO_4$), filtered, and concentrated under reduced pressure. The crude material was purified by column chromatography on $SiO_2$ (10-30% EtOAc-hexanes, elution was observed at 285 nm and 228 nm). The product first intermediate 12 was a colorless, foul-smelling oil that existed at 26° C. as a 60:40 mixture of rotamers in solution (66%): $^1$H NMR ($CDCl_3$) δ 0.82 (apparent t, J=7.6 Hz, 6H), 1.42 (s, 9H), 1.70 (apparent sept, J=6.62 Hz, 1H), 2.08-2.15 (m, 1H), 2.15-2.24 (m, 1H), 2.62-2.70 (m, 1H), 2.75-2.91 (m, 1H), 2.93-3.07 (m, 1H), 3.07-3.29 (m, 1.6H), 3.30-3.43 (m, 0.4H), 3.79 (s, 3H), 3.81 (s, 3.4H), 4.04-4.16 (m, 0.6H), 5.52-5.62 (m, 1H), 5.69 (s, 1H), 5.90 (s, 0.6H), 6.04 (s, 0.4H), 6.57 (s, 1H), 6.63 (s, 1H); $^{13}$C NMR ($CDCl_3$) δ 22.45, 27.04, 27.25, 28.11, 28.41, 38.01, 39.33, 40.39, 45.20, 45.90, 51.62, 55.92, 55.98, 79.75, 80.23, 109.85, 110.25, 110.28, 111.41, 125.65, 125.72, 126.26, 129.25, 147.57, 147.87, 148.16, 148.29, 148.35, 154.40, 154.51, 199.53; HRMS-(ESI+) calcd for ($C_{24}H_{35}NO_5$)+H) [M+H]$^+$ 418.2594. found 418.2590.

Method 8 Oxidation of Allylic Alcohol 8 to Provide First Intermediate 13

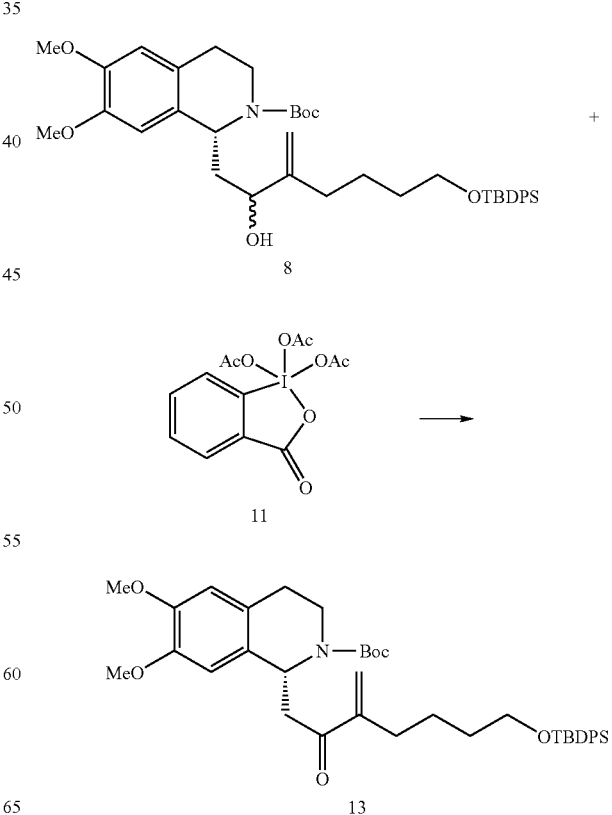

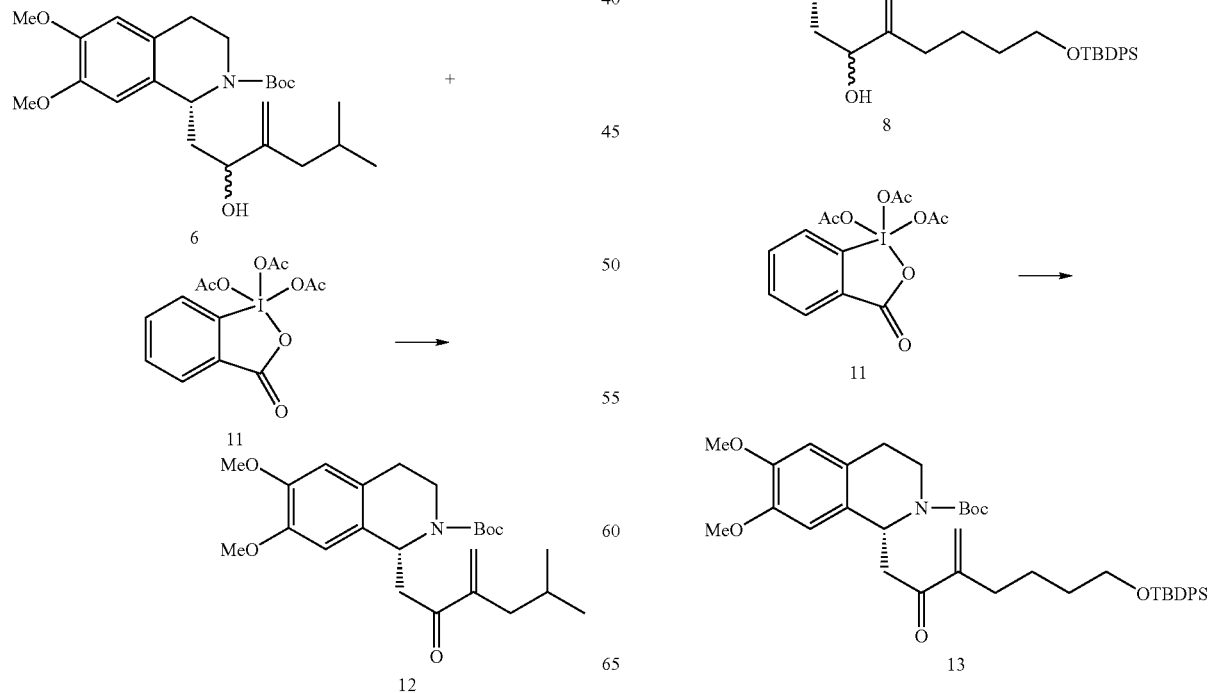

To a 0.1 M solution of 8 (1.0 eq) in dichloromethane at 0° C. was added 1.1 eq. of the Dess-Martin reagent 11. The reaction mixture was allowed to stir, slowly warming to room temperature over 2.5 h. The reaction was quenched by the addition of saturated aqueous sodium bicarbonate solution and diluted with dichloromethane. The organic and aqueous layers were partitioned and separated and the aqueous layer extracted with three additional portions of dichloromethane. The combined organic extracts were washed with brine, dried (MgSO$_4$), filtered, and concentrated under reduced pressure. The crude material was purified by column chromatography on SiO$_2$ (10-50% EtOAc-hexanes, elution was observed at 285 nm and 228 nm). The product first intermediate 13 was a colorless, oil that existed at 26° C. as a 50:50 mixture of rotamers in solution (82%): $^1$H NMR (CD$_2$Cl$_2$) δ 1.19 (s, 9H), 1.55 (s, 9H), 1.63-1.83 (m, 5H), 2.34-2.57 (m, 2H), 2.70-2.85 (m, 1H), 2.85-3.05 (m, 1H), 3.05-3.41 (m, 2.5H), 3.41-3.56 (m, 0.5H), 3.81-3.83 (m, 1H), 3.84 (s, 3H), 3.86 (s, 3H), 3.97-4.08 (m, 0.5H), 4.20-4.35 (m, 0.5H), 5.68 (apparent t, J=6.6 Hz, 1H), 5.87 (s, 1H), 6.09 (s, 0.5H), 6.19 (s, 0.5H), 6.71 (s, 1H), 6.76 (s, 1H), 7.45-7.60 (m, 6H), 7.77-7.95 (m, 4H); $^{13}$C NMR (CD$_2$Cl$_2$) δ 19.19, 24.66, 24.75, 26.83, 28.06, 28.28, 30.57, 32.43, 37.75, 39.20, 45.16, 45.66, 63.84, 79.46, 79.77, 110.21, 110.49, 111.81, 124.37, 124.67, 126.45, 127.76, 129.19, 129.68, 134.13, 135.61, 147.79, 148.19, 149.20, 154.09, 154.41, 199.15, 199.27; HRMS-(ESI+) calcd for (C$_{40}$H$_{53}$NO$_6$Si+H) [M+H]$^+$ 672.3720, found 672.3715.

Method 9 Oxidation of allylic Alcohol 10 to Provide First Intermediate 14

To a 0.1 M solution of allylic alcohol 10 (1.0 eq) in dichloromethane at 0° C. was added 1.1 eq. of the Dess-Martin reagent 11. The reaction mixture was allowed to stir, slowly warming to room temperature over 5 h. The reaction was quenched by the addition of saturated aqueous sodium bicarbonate solution and diluted with dichloromethane. The organic and aqueous layers were partitioned and separated and the aqueous layer extracted with three additional portions of dichloromethane. The combined organic extracts were washed with brine, dried (MgSO$_4$), filtered, and concentrated under reduced pressure. The crude material was purified by column chromatography on SiO$_2$ (10-50% EtOAc-hexanes, elution was observed at 285 nm and 228 nm). The product first intermediate 14 was a yellow foam that existed at 26° C. as a 50:50 mixture of rotamers in solution (93%): $^1$H NMR (CD$_2$Cl$_2$) δ 0.85 (s, 6H), 1.14 (s, 9H), 1.48-1.57 (m, 9H), 1.65 (t, J=7.3 Hz, 2H), 2.30-2.50 (m, 2H), 2.70-2.80 (m, 1H), 2.85-2.98 (m, 1H), 3.07-3.17 (m, 1H), 3.22-3.37 (m, 1.5H), 3.38-3.50 (m, 0.5H), 3.81 (s, 3H), 3.85 (s, 3H), 3.85-3.92 (m, 2H), 3.94-4.02 (m, 0.5H), 4.18-4.25 (m, 0.5H), 5.65-5.72 (m, 1H), 5.74 (s, 1H), 6.07 (s, 0.5H), 6.14 (s, 0.5H), 6.69 (s, 1H), 6.76 (s, 1H), 7.45-7.54 (m, 6H), 7.77-7.82 (m, 4H); $^{13}$C NMR (CD$_2$Cl$_2$) δ 19.09, 26.80, 26.92, 26.97, 28.13, 28.22, 28.28, 33.22, 37.94, 39.39, 41.79, 41.87, 44.49, 45.33, 46.02, 51.16, 51.44, 55.79, 55.83, 61.05, 79.47, 79.76, 110.18, 110.51, 111.74, 126.40, 127.26, 127.36, 127.76, 129.48, 129.69, 134.09, 135.66, 146.93, 147.06, 147.78, 148.10, 154.16, 154.47, 199.36; HRMS-(ESI+) calcd for (C$_{42}$H$_{57}$NO$_6$Si—C$_5$H$_9$O$_2$(Boc)+H) [M-Boc+H]$^+$ 600.3509. found 600.3496.

Method 10 Removal the Boc Protecting Group from First Intermediate 12 and Amino Cyclization Provide (+)-Tetrabenazine 15

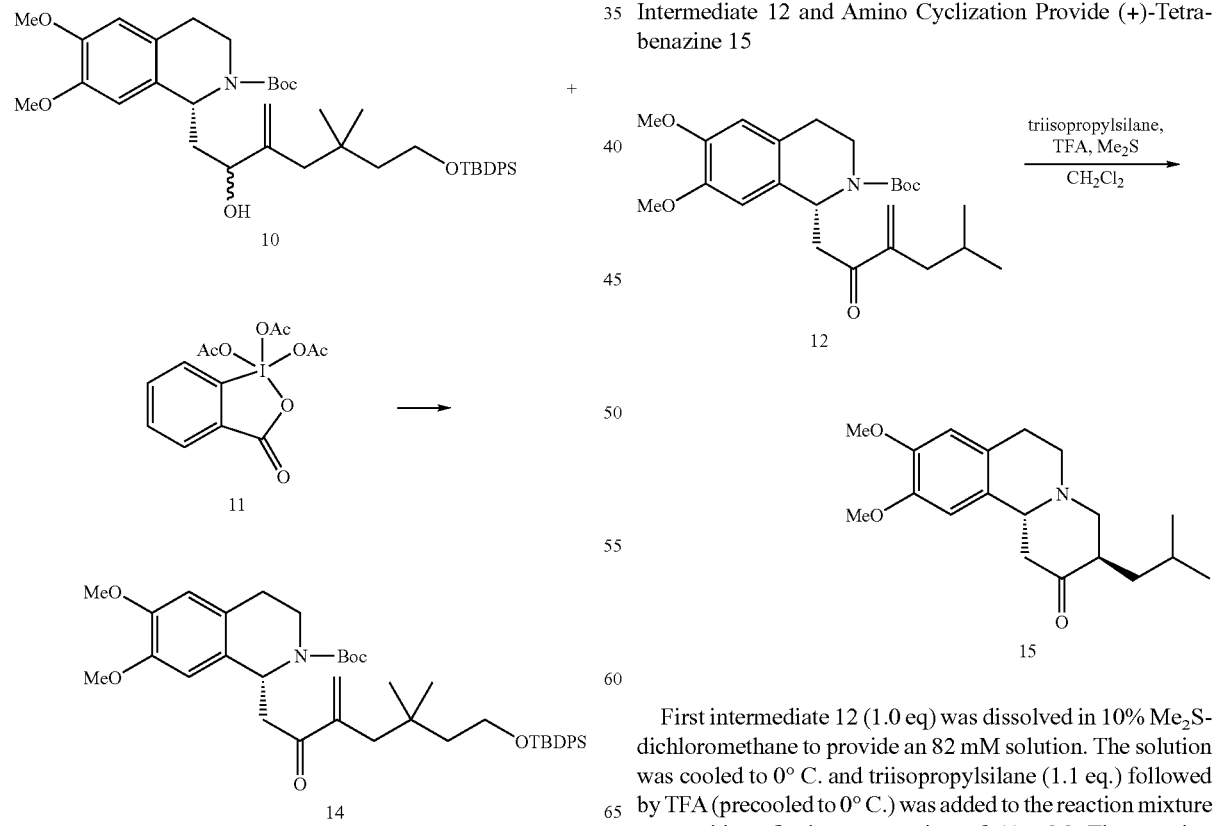

First intermediate 12 (1.0 eq) was dissolved in 10% Me$_2$S-dichloromethane to provide an 82 mM solution. The solution was cooled to 0° C. and triisopropylsilane (1.1 eq.) followed by TFA (precooled to 0° C.) was added to the reaction mixture to provide a final concentration of 41 mM. The reaction mixture was permitted to stir at 0° C. for 1 h. Following the allotted time the reaction mixture was quenched at 0° C. by the addition of saturated aqueous potassium carbonate solution and concentrated under reduced pressure to remove the majority of the dimethylsulfide. The mixture was extracted with five portions of dichloromethane, and the combined organic extracts were washed with brine, dried (MgSO$_4$), filtered and concentrated under reduced pressure to provide the crude product as a yellow solid. The crude product was recrystallized from 3.5% dimethoxyethane in hexanes. The resulting colorless crystals were washed with hexanes to provide pure (+)-tetrabenazine (15) 46%: mp 126.0° C. (3.5% DME-hexanes) (a crystal polymorph was observed at 116° C.); $[\alpha]^{26}_D$ +37.2 (c 0.41, CH$_2$Cl$_2$); $^1$H NMR (CD$_2$Cl$_2$) δ 0.89 (apparent t, J=7.2 Hz, 6H), 0.98 (ddd, J=12, 6.0, 4.0 Hz, 1H), 1.59-1.68 (m, 1H), 1.74 (ddd, J=12, 5.9, 5.7 Hz, 1H), 2.32 (apparent t, J=11.7 Hz, 1H), 2.46 (apparent t, J=12.3 Hz, 1H), 2.55 (ddd, J=12, 10.0, 3.8 Hz, 1H), 2.65-2.73 (m, 2H), 2.83 (dd, J=5.5, 2.8 Hz, 1H), 2.97-3.07 (m, 1H), 3.07-3.14 (m, 1H), 3.25 (dd, J=9.7, 6.3 Hz, 1H), 3.47 (apparent d, J=12 Hz, 1H), 3.75 (s, 3H), 3.77 (s, 3H), 6.55 (s, 1H), 6.60 (s, 1H) $^{13}$C NMR (CD$_2$Cl$_2$) δ 21.98, 23.02, 25.51, 29.46, 35.16, 47.47, 47.63, 50.47, 55.87, 56.01, 61.47, 62.46, 108.46, 111.72, 126.37, 128.96, 147.65, 147.98, 209.72; HRMS-(ESI+) calcd for (C$_{19}$H$_{27}$NO$_3$+H) [M+H]$^+$ 318.2069, found 318.2082.

Method 11 Removal the Boc Protecting Group from First Intermediate 13 and Amino Cyclization Provide (+)-TBZ Compound 16 of 13 mM. The reaction mixture was permitted to stir at 0° C. for 1 h. Following the allotted time the reaction mixture was quenched at 0° C. by the addition of saturated aqueous potassium carbonate solution and concentrated under reduced pressure to remove the majority of the dimethylsulfide. The mixture was extracted with five portions of dichloromethane, and the combined organic extracts were washed with brine, dried (MgSO$_4$), filtered and concentrated under reduced pressure to provide an orange oil. The isolated material was immediately subjected to purification by flash chromatography on SiO$_2$ (20-30% EtOAc-hexanes, elution was observed at 285 nm and 228 nm). The semipure product (existed as a mixture of diastereomers heavily favoring the desired product) was subjected to crystallization from 3.5% dimethoxyethane in hexanes over several days. The resulting colorless crystals were washed with hexanes to provide (+)-TBZ compound 16 as a single diastereomer 42%: $[\alpha]^{26}_D$ +40.1 (c 0.63, CH$_2$Cl$_2$); $^1$H NMR (CD$_2$Cl$_2$) δ 1.14 (s, 9H), 1.18-1.30 (m, 1H), 1.45-1.56 (m, 2H), 1.60-1.75 (m, 2H), 1.86-1.98 (m, 1H), 2.41 (apparent t, J=11.4 Hz, 1H), 2.47 (apparent t, J=12.6 Hz, 1H), 2.59-2.82 (m, 3H), 2.93 (dd, J=13.1, 2.8 Hz, 1H), 3.06-3.20 (m, 2H), 3.34 (dd, J=9.6, 6.1 Hz, 1H), 3.55 (apparent d, J=11.6 Hz, 1H), 3.78 (apparent t, J=6.3 Hz, 2H), 3.84 (s, 3H), 3.85 (s, 3H), 6.64 (s, 1H), 6.69 (s, 1H), 7.40-7.53 (m, 6H), 7.70-7.81 (m, 4H); $^{13}$C NMR (CD$_2$Cl$_2$) δ 19.14,

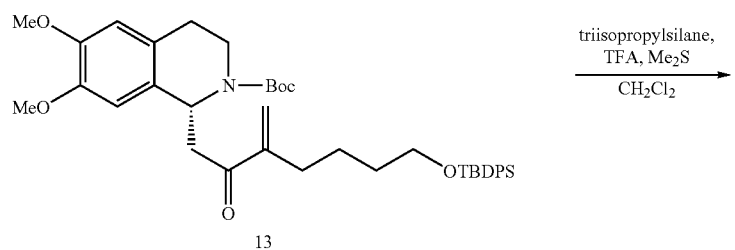

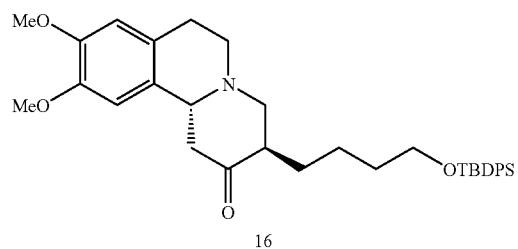

The first intermediate starting material 13 (1.0 eq) was dissolved in 10% Me$_2$S-dichloromethane to provide an 26 mM solution. The solution was cooled to 0° C. and triisopropylsilane (1.1 eq.) followed by TFA (precooled to 0° C.) was added to the reaction mixture to provide a final concentration 23.43, 25.98, 26.74, 29.47, 32.77, 47.55, 49.42, 50.44, 55.74, 55.86, 61.06, 62.36, 63.81, 108.31, 111.68, 126.31, 127.68, 128.91, 129.60, 134.15, 135.59, 147.59, 147.90, 209.36; HRMS-(ESI+) calcd for (C$_{35}$H$_{45}$NO$_4$Si+H) [M+H]$^+$ 572.3196. found 572.3187.

Method 12 Removal the Boc Protecting Group from First Intermediate 14 and Amino Cyclization Provide (+)-TBZ Compound 17

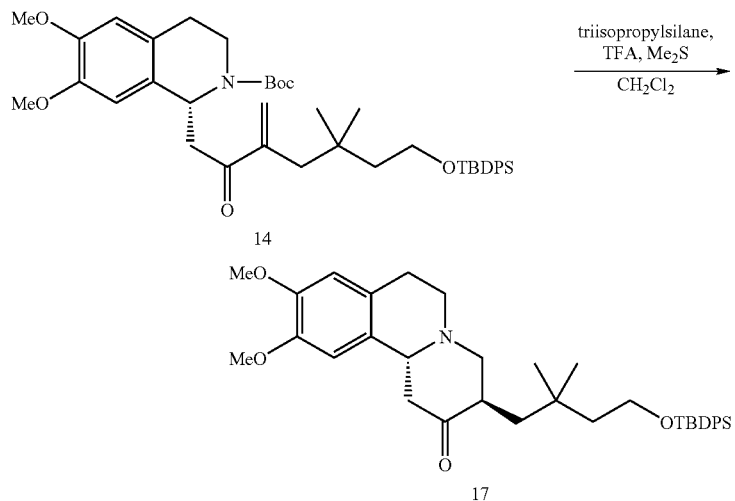

The starting material 14 (1.0 eq) was dissolved in 10% Me₂S-dichloromethane to provide a 176 mM solution of the starting material. The solution was cooled to 0° C. and triisopropylsilane (1.1 eq.) followed by TFA (precooled to 0° C.) was added to the reaction mixture to provide a final concentration of 88 mM. The reaction mixture was permitted to stir at 0° C. for 1 h. Following the allotted time the reaction mixture was quenched at 0° C. by the addition of saturated aqueous potassium carbonate solution and concentrated under reduced pressure to remove the majority of the dimethylsulfide. The mixture was extracted with five portions of dichloromethane, and the combined organic extracts were washed with brine, dried (MgSO₄), filtered and concentrated under reduced pressure to provide a yellow foam. The crude product was purified by flash chromatography on SiO₂ (0.2% triethylamine-10% EtOAc-89.8% hexanes to 0.2% triethylamine-50% EtOAc-49.8% hexanes, elution was observed at 285 nm and 228 nm). The product (+)-TBZ compound 17 was a colorless foam consisting of only the desired diastereomer 73%: ¹H NMR (CD₂Cl₂) δ 0.79 (dd, J=13.8, 3.8 Hz, 1H), 0.92 (s, 6H), 1.14 (s, 9H), 1.59-1.72 (m, 2H), 2.27 (dd, J=13.2, 5.1 Hz, 1H), 2.52-2.65 (m, 2H), 2.68-2.82 (m, 2H), 2.94 (dd, J=13.0, 3.0 Hz, 1H), 3.06-3.18 (m, 2H), 3.25 (dd, J=9.8, 6.3 Hz), 3.55 (dd, J=11.6, 1.8 Hz, 1H), 3.83-3.88 (m, 8H), 6.65 (s, 1H), 6.69 (s, 1H), 7.44-7.53 (m, 6H), 7.74-7.82 (m, 4H); ¹³C NMR (CD₂Cl₂) δ 19.09, 26.79, 27.10, 29.48, 32.31, 36.90, 44.38, 46.02, 47.45, 50.15, 55.77, 55.91, 61.09, 62.53, 63.50, 108.38, 111.75, 126.30, 127.74, 128.93, 129.67, 134.13, 135.65, 147.66, 147.98, 208.73; HRMS-(ESI+) calcd for (C₃₇H₄₉NO₄Si+H) [M+H]⁺ 600.3509, found 600.3499.

Method 13 Reduction of (+)-Tetrabenazine 15 to a Diastereomeric Mixture of Dihydrotetrabenazine Compounds 18 and 19

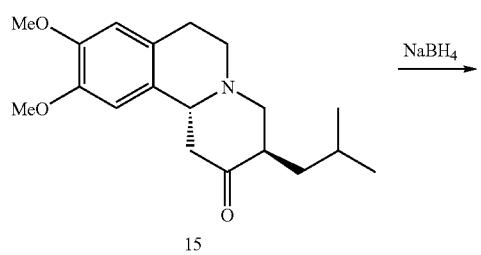

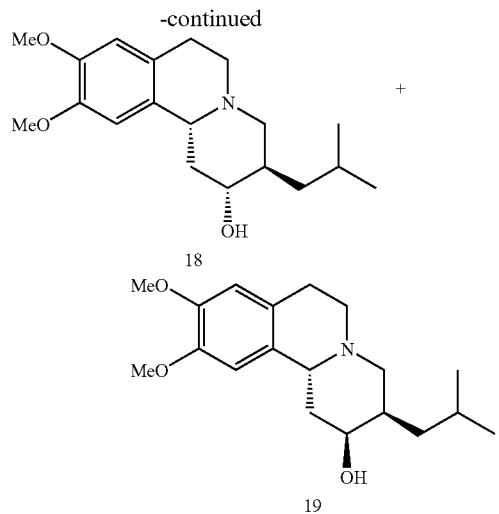

To a 0.11 M solution of (+)-TBZ (15) in ethanol at 0° C. was added NaBH₄ (2.85 eq). The reaction mixture was allowed to stir for 60 min. at room temperature. The solvent was carefully removed under reduced pressure, and the residue was taken up in dichloromethane and washed with three portions of saturated aqueous K₂CO₃. The aqueous washings were back extracted with two portions of dichloromethane. The combined organic extracts were dried (MgSO₄), filtered, and concentrated under reduced pressure to provide a colorless oil that crystallized on standing under high vacuum. Purification of the crude product was achieved by chromatography on SiO₂ (2.5-5% MeOH—CH₂Cl₂, elution was observed at 285 nm) UV active fractions were reanalyzed by TLC. Two products, 18 and 19, were isolated from this procedure. The major product 18 was a colorless solid 74%: [α]²⁶_D +48 (c 0.30, CH₂Cl₂) ¹H NMR (CD₂Cl₂) δ 0.93 (d, J=6.6 Hz, 3H), 0.95 (d, J=6.6 Hz, 3H), 1.04 (ddd, J=14.6, 8.7, 4.3 Hz, 1H), 1.42 (dd, J=20.2, 11.4 Hz, 1H), 1.59 (ddd, J=13.7, 9.6, 3.3 Hz, 1H), 1.64-1.78 (m, 2H), 1.96 (apparent t, J=11.4 Hz, 1H), 2.27 (br s, 1H), 2.40-2.48 (m, 1H), 2.54 (ddd, J=12.3, 3.7, 2.3 Hz, 1H), 2.60-2.67 (m, 1H), 2.95-3.09 (m, 3H), 3.11 (apparent d, J=11.1 Hz, 1H), 3.35 (ddd, J=10.4, 10.4, 4.5 Hz, 1H), 3.80-3.81 (m, 6H), 6.60 (s, 1H), 6.69 (s, 1H); $^{13}$C NMR (CD$_2$Cl$_2$) δ 21.61, 24.02, 25.33, 29.30, 39.68, 40.81, 41.58, 51.83, 55.74, 55.91, 60.02, 60.92, 74.32, 108.42, 111.73, 126.68, 129.76, 147.35, 147.61; HRMS-(ESI+) calcd for (C$_{19}$H$_{29}$NO$_3$+H) [M+H]$^+$ 320.2226. found 320.2242. The minor product 19 was a yellow oil 4%: $^1$H NMR (CD$_2$Cl$_2$) δ 0.94 (d, J=6.6 Hz, 3H), 0.96 (d, J=6.6 Hz, 3H), 1.13-1.20 (m, 1H), 1.24-1.34 (m, 2H), 1.60-1.77 (m, 2H), 1.89-2.00 (m, 1H) 2.36-2.44 (m, 2H), 2.53 (ddd, J=10.5, 10.5, 3.8 Hz, 1H), 2.58-2.70 (m, 2H), 2.91-2.98 (m, 1H), 2.98-3.09 (m, 1H), 3.48 (apparent d, J=11.6 Hz, 1H), 3.80-3.82 (apparent s, 6H), 4.07 (apparent d, J=3.1 Hz, 1H), 6.60 (s, 1H), 6.68 (s, 1H); $^{13}$C NMR (CD$_2$Cl$_2$) δ 22.74, 22.81, 24.87, 29.30, 37.83, 38.87, 39.42, 52.44, 55.76, 55.96, 56.32, 56.43, 67.88, 108.45, 111.78, 127.18, 130.38, 147.30, 147.54.

Method 14 Ketalization of TBZ Compound 16

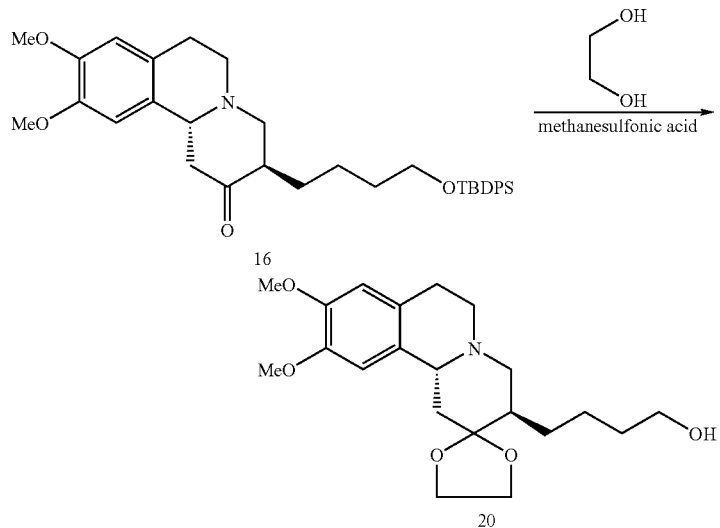

To an 87 mM solution of the starting material 16, 1.0 eq) in ethylene glycol was added methane sulfonic acid (1.76 eq). The reaction mixture was heated to and maintained at 85° C. for 20 h in a sealed vessel. Following the allotted time, the reaction mixture was quenched be the addition of 1 mL of saturated aqueous potassium carbonate solution and EtOAc was added. The reaction mixture was stirred for an additional hour at room temperature after which time the aqueous and organic layers were partitioned and separated. The aqueous layer was extracted with three portions of CH$_2$Cl$_2$ and the combined organic extracts were dried (MgSO$_4$), filtered, and concentrated under reduced pressure to provide a yellow oil. Purification of the crude material was undertaken by flash chromatography on SiO$_2$ (1% triethylamine-DCM to 1% triethyamine-9% methanol-90% DCM; elution was observed at 284 nm and 240 nm). Pools believed to contain the desired product were collected to provide ketal 20 as a colorless oil 73%: $^1$H NMR (CD$_2$Cl$_2$) δ 1.03-1.15 (m, 1H), 1.20-1.35 (m, 2H), 1.37-1.61 (m, 4H), 1.87-1.99 (m, 1H), 2.08-2.17 (br. s, 1H), 2.20-2.29 (m, 2H), 2.42-2.51 (m, 1H), 2.55-2.64 (m, 1H), 2.92-3.03 (m, 3H), 3.27 (apparent d, J=11 Hz, 1H), 3.57 (apparent t, J=6.3 Hz, 2H), 3.758 (s, 3H), 3.764 (s, 3H), 3.92-4.00 (m, 2H), 4.00-4.09 (m, 2H), 6.56 (s, 1H), 6.57 (s, 1H); $^{13}$C NMR (CD$_2$Cl$_2$) δ 23.74, 25.30, 29.31, 33.25, 41.00, 43.90, 55.74, 56.07, 58.68, 59.82, 62.64, 63.68, 65.17, 63.35, 108.50, 109.65, 111.78, 126.82, 129.81, 147.31, 147.67; LRMS-(ESI+) calcd for (C$_{21}$H$_{31}$NO$_5$+H) [M+H]$^+$ 378.23, found 378.25.

Method 15 Fluorination of Hydroxy Ketal 20

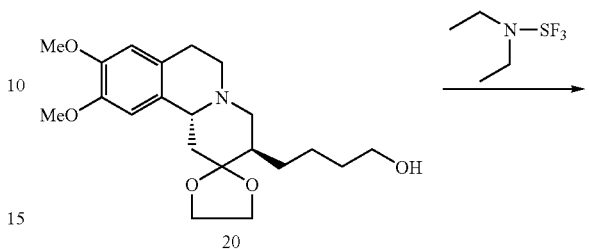

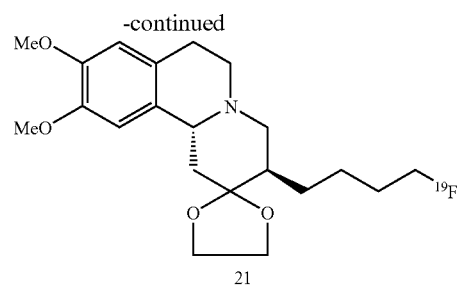

To a 100 mM solution of the starting hydroxy ketal 20 in dichloromethane was added DAST reagent (2.2 eq.) at room temperature. The reaction mixture was permitted to stir for 16 h after which time the reaction mixture was quenched by the addition of saturated aqueous NaHCO$_3$. The aqueous and organic layers were partitioned and separated, and the aqueous layer was extracted with three portions of dichloromethane. The combined organic extracts were dried (MgSO$_4$), filtered, and concentrated under reduced pressure to provide a yellow oil that was purified by flash chromatography on SiO$_2$ (1% triethylamine-DCM to 1% triethyamine-5% methanol-94% DCM, 40 CV; elution was observed at 284 nm and 240 nm). The purified product alpha-fluoroalkyl ketal 21 was obtained as a yellow oil in 60% yield. The isolated material was taken on to the next step without additional characterization.

Example 1

Preparation of Alpha-Fluoroalkyl Tetrabenazine Compound 22 Via Protected Tetrabenazine Compound Alpha-Fluoroalkyl Ketal 21

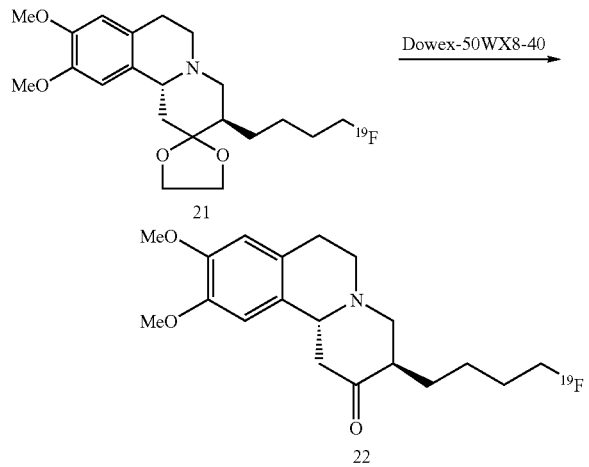

To an 8 mM solution of the starting fluoroalkyl ketal 21 in 3:1 THF-water was added 0.18 g of DOWEX strongly acidic cation exchange resin. The reaction mixture was heated to and maintained at 65° C. overnight. The resin was washed with saturated aqueous potassium carbonate and the mixture was extracted with three portions of dichloromethane and three portions of toluene. The organic extracts were combined, dried (MgSO$_4$), filtered, and concentrated under reduced pressure. The crude material was purified by semi-preparative HPLC on a Phenomenex Gemini C$_{18}$ column 5 µm, (4.6×250 mm; UV @ 284 nm and 240 nm) at a Flow rate of 1.0 mL/min. The following gradient was used: 100% 0.1 mM TEAA buffer pH 7.0 and holding for 3 min. then ramping to 98% MeCN 2% 0.1 mM TEAA buffer pH 7.0 over 25 min and finally holding at this level for an additional 12 min. The column was maintained at room temperature during the analysis. The major UV active peak eluted at 34.8 min and was collected and concentrated under reduced pressure to provide the product as a yellow oil 5%: LRMS-(ESI+) calcd for (C$_{19}$H$_{26}$FNO$_3$+H) [M+H]$^+$ 336.20. found 336.16.

Method 16 Preparation of Dihydrotetrabenazine Compound 23

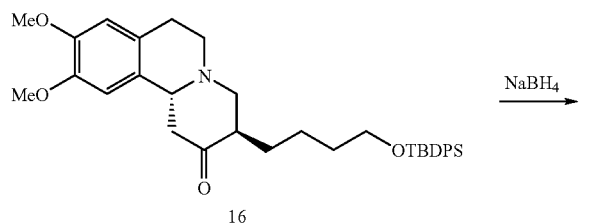

To a 0.1 M solution of tetrabenazine compound 16 in ethanol at 0° C. was added NaBH$_4$ (2.85 eq). The reaction mixture was allowed to stir for 60 min. at room temperature. The excess solvent was carefully removed under reduced pressure, and the residue was taken up in dichloromethane and washed with three portions of saturated aqueous K$_2$CO$_3$. The aqueous washings were back extracted with two portions of dichloromethane. The combined organic extracts were dried (MgSO$_4$), filtered, and concentrated under reduced pressure to provide a yellow foam. Purification of the crude product was achieved by chromatography on SiO$_2$ (2.5-5% MeOH—CH$_2$Cl$_2$, elution was observed at 285 nm). The product dihydrotetrabenazine compound 23 was a colorless foam 78%: $^1$H NMR (CD$_2$Cl$_2$) δ 1.09-1.22 (m, 1H), 1.44 (dd, J=20.1, 11.6 Hz, 2H), 1.55-1.72 (m, 4H), 1.78-1.88 (m, 1H), 2.02 (apparent t, J=11.4 Hz, 1H), 2.46 (ddd, J=4.6, 11.3, 10.3 Hz, 1H), 2.57 (ddd, J=13.1, 3.8, 2.5 Hz, 1H), 2.65 (dd, J=14.3, 4.0 Hz, 1H), 2.94-3.10 (m, 3H), 3.14 (apparent d, J=11.1 Hz, 1H), 3.40 (ddd, J=9.5, 9.5, 4.6 Hz, 1H), 3.76 (apparent t, J=6.3 Hz, 2H), 3.83 (apparent s, 6H), 6.63 (s, 1H), 6.73 (s, 1H), 7.42-7.49 (m, 6H), 7.71-7.76 (m, 4H), $^{13}$C NMR (CD$_2$Cl$_2$) δ 19.17, 23.21, 26.75, 29.38, 29.79, 33.03, 40.89, 43.88, 51.86, 55.76, 55.94, 59.78, 60.95, 63.93, 73.92, 108.48, 111.76, 126.75, 127.69, 129.61, 129.81, 134.23, 135.62, 147.38, 147.63; HRMS-(ESI+) calcd for (C$_{35}$H$_{47}$NO$_4$Si+H) [M+H]$^+$ 574.3353, found 574.3333.

Method 17 Preparation of Dihydrotetrabenazine Compound 24 and 2-epi-24

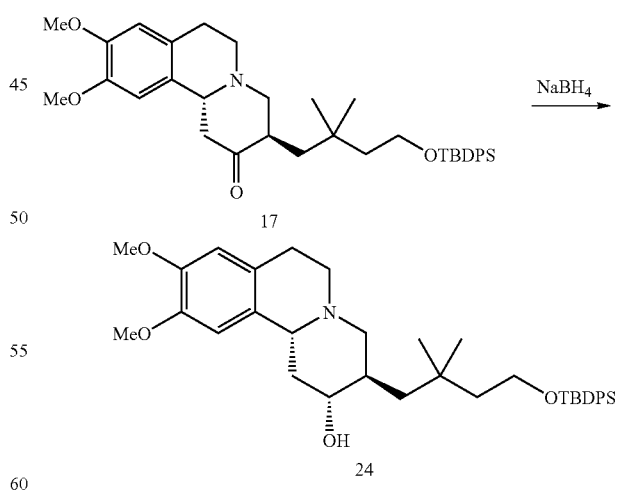

To a 0.1 M solution of tetrabenazine compound 17 in ethanol at 0° C. was added NaBH$_4$ (2.85 eq). The reaction mixture was allowed to stir for 60 min. at room temperature. The excess solvent was carefully removed under reduced pressure, and the residue was taken up in dichloromethane and washed with three portions of saturated aqueous K$_2$CO$_3$.

The aqueous washings were back extracted with two portions of dichloromethane. The combined organic extracts were dried (MgSO$_4$), filtered, and concentrated under reduced pressure to provide a yellow foam. Purification of the crude product dihydrotetrabenazine compound 24 was achieved by chromatography on SiO$_2$ (2.5-5% MeOH—CH$_2$Cl$_2$, elution was observed at 285 nm). The product 24 was a colorless foam 69%: $^1$H NMR (CD$_2$Cl$_2$) δ 0.99 (s, 6H), 1.02-1.06 (m, 1H), 1.16 (s, 9H), 1.48 (dd, J=20.2, 11.4 Hz, 1H), 1.63-1.82 (m, 4H), 2.06 (apparent t, J=11.4 Hz, 1H), 2.47 ((ddd, J=3.8, 10.6, 10.6 Hz, 1H), 2.60 (ddd, J=12.0, 3.4, 2.3 Hz, 1H), 2.68 (apparent br d, J=15.4 Hz, 1H), 2.96-3.04 (m, 1H), 3.05-3.14 (m, 2H), 3.17 (apparent br d, J=11.4 Hz, 1H), 3.31 (ddd, J=9.3, 9.3, 4.3 Hz, 1H), 3.85 (s, 6H), 3.87-3.92 (m, 2H), 6.66 (s, 1H), 6.75 (s, 1H), 7.43-7.56 (m, 6H), 7.76-7.86 (m, 4H); $^{13}$C NMR (CD$_2$Cl$_2$) δ 19.10, 26.83, 27.67, 27.77, 29.28, 32.73, 39.98, 40.64, 42.21, 44.66, 49.89, 51.75, 55.77, 55.94, 61.02, 61.24, 62.71, 73.88, 108.46, 111.79, 126.62, 127.76, 129.70, 134.10, 135.68, 147.44, 147.69. A small amount of the ring position-2 epimer of dihydrotetrabenazine compound 24 was isolated in about 12% yield and was characterized. The epimeric product, 2-epi-24, was a pale yellow oil: $^1$H NMR (CD$_2$Cl$_2$) δ 0.92 (s, 6H), 0.96-1.02 (m, 2H), 1.08 (s, 9H), 1.42 (dd, J=14.5, 4.7 Hz, 1H), 1.61-1.71 (m, 3H), 1.86-1.95 (m, 1H), 2.35 (apparent dt, J=13.7, 2.9 Hz, 1H), 2.43 (apparent t, J=11.6 Hz, 1H), 2.51 (ddd, J=11.4, 11.4, 3.9 Hz, 1H), 2.59-2.67 (m, 2H), 2.88-2.95 (m, 1H), 2.98-3.11 (m, 1H), 3.45 (br d, J=11.4 Hz, 1H), 3.76-3.88 (m, 8H), 3.94-4.01 (m, 1H), 6.61 (s, 1H), 6.67 (s, 1H), 7.40-7.54 (m, 6H), 7.68-7.81 (m, 4H); $^{13}$C NMR (CD$_2$Cl$_2$) δ 19.05, 26.72, 27.51, 29.31, 29.78, 32.81, 36.51, 39.36, 41.99, 44.53, 52.34, 55.77, 55.86, 55.96, 57.71, 61.16, 69.62, 108.45, 111.80, 127.19, 127.71, 129.64, 130.43, 134.12, 135.65, 147.30, 147.53. The minor epimer, 2-epi-24, was converted by a series of steps analogous to Method steps 19 (protection of the hydroxy methine group as a THP ether to provide 2-epi-26), 21 (removal of the t-butyldiphenylsilyl group to provide 2-epi-28), and 23 (reaction of the primary hydroxy group with DAST to provide 2-epi-30); and then removal of the THP ether protecting group in a step analogous to that described in Example 3 to provide the alpha-fluoroalkyl dihydrotetrabenazine 2-epi-32 (See Table 15), a compound identical in structure to compound 32 in all respects save the configuration at ring position-2 which is "S" rather than "R". The intermediate 2-epi-28 was characterized by low resolution mass spectroscopy: LRMS-(ESI+) calcd for (C$_{24}$H$_{37}$NO$_5$+H) [M+H]$^+$ 448.31. found 448.26. Alpha-fluoroalkyl dihydrotetrabenazine 2-epi-32 was characterized by high resolution mass spectroscopy: HRMS-(ESI+) calcd for (C$_{21}$H$_{32}$FNO$_3$+H) [M+H]$^+$ 366.24445, found 366.24333.

Method 18 Preparation of THP Protected DTBZ Compound 25

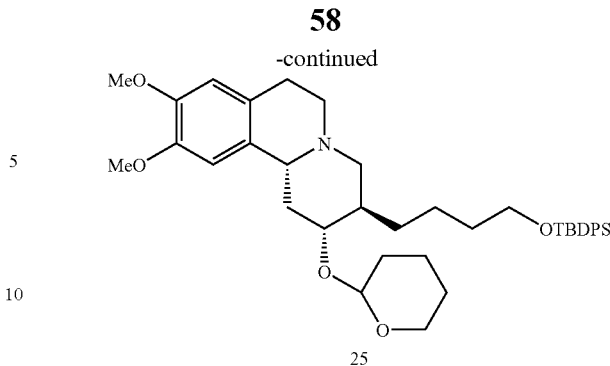

25

To a 0.1M solution of the starting dihydrotetrabenazine compound 23 (1.0 eq) in dichloromethane was added methanesulfonic acid (1.1 eq), followed by dihydropyran (2.2 eq.). The reaction was permitted to stir at 26° C. for 36 h. Following this time, the reaction mixture was quenched by the addition of saturated aqueous potassium carbonate solution. Dichloromethane was added, and the aqueous and organic layers were partitioned and separated. The aqueous layer was extracted with three portions of CH$_2$Cl$_2$, and the combined organic extracts were dried, (MgSO$_4$), filtered, and concentrated under reduced pressure to provide a yellow oil that was immediately subjected to purification by flash chromatography on SiO$_2$ (1% triethylamine-DCM to 1% triethyamine-5% methanol-94% DCM; elution was observed at 284 nm and 240 nm). Fractions presumed to contain the desired product were concentrated under reduced pressure to provide protected dihydrotetrabenazine compound 25 as a pale yellow oil that existed as a roughly 1:1 mixture of diastereomers 75%: $^1$H NMR (CD$_2$Cl$_2$) δ 1.10 (s, 9H), 1.48-1.65 (m, 8H), 1.66-1.79 (m, 4H), 1.80-1.90 (m, 1.5H), 1.91-1.99 (m, 0.5H), 1.99-2.11 (m, 1H), 2.40-2.51 (m, 1H), 2.62-2.68 (m, 1H), 2.68-2.76 (m, 1H), 2.95-3.16 (m, 3H), 3.29-3.37 (m, 0.5H), 3.49-3.58 (m, 1.5H), 3.71-2.78 (dd, J=9.4, 6.1 Hz, 2H); 3.79-3.86 (m, 6H), 3.86-3.94 (m, 1H), 3.95-4.07 (m, 1H), 4.65-4.71 (m, 0.5H), 4.92-5.01 (m, 0.5H), 6.60-6.64 (s, 1H), 6.69-6.72 (s, 0.5H), 6.72-6.75 (s, 0.5H), 7.39-7.50 (m, 6H), 7.68-7.77 (m, 4H); $^{13}$C NMR (CD$_2$Cl$_2$) δ 19.16, 19.69, 20.24, 23.17, 23.23, 25.65, 25.67, 25.72, 26.74, 29.43, 29.46, 29.78, 29.90, 30.69, 31.14, 31.21, 33.06, 33.11, 36.00, 39.52, 41.61, 42.49, 51.77, 51.95, 55.76, 56.04, 56.17, 59.91, 59.99, 60.72, 61.00, 62.31, 62.50, 62.87, 63.96, 64.10, 75.58, 82.46, 94.06, 101.79, 108.75, 108.80, 111.76, 111.82, 126.83, 126.98, 127.68, 129.58, 130.00, 130.04, 134.23, 134.25, 134.26, 134.28, 135.61, 147.35, 147.38, 147.68, 147.71

Method 19 Preparation of THP Protected DTBZ Compound 26

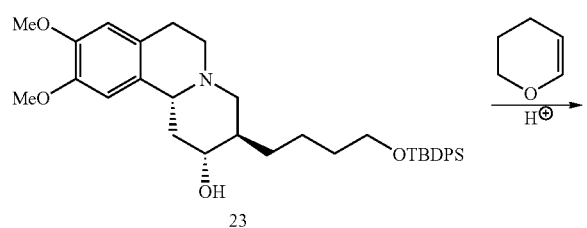

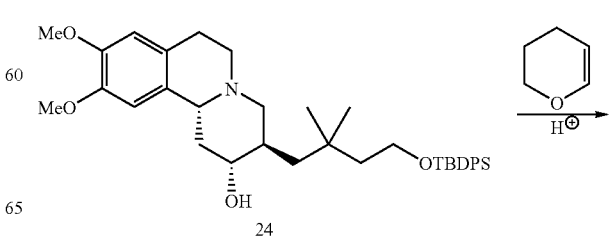

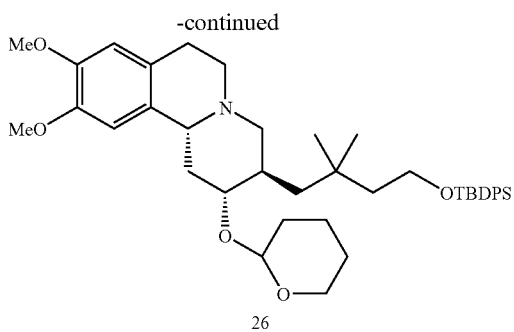

26

To a 0.1M solution of the starting dihydrotetrabenazine compound 24 (1.0 eq) in dichloromethane was added methanesulfonic acid (1.1 eq), followed by dihydropyran (2.2 eq.). The reaction was permitted to stir at 26° C. for 36 h. Following this time, the reaction mixture was quenched be the addition of saturated aqueous potassium carbonate solution. Dichloromethane was added, and the aqueous and organic layers were partitioned and separated. The aqueous layer was extracted with three portions of $CH_2Cl_2$, and the combined organic extracts were dried, ($MgSO_4$), filtered, and concentrated under reduced pressure to provide protected dihydrotetrabenazine compound 26 as a yellow foam that existed as a roughly 1:1 mixture of diastereomers the crude product was taken on to the next step without additional purification 99%.

Method 20 Preparation of Alpha-Hydroxyalkyl Protected Dihydrotetrabenazine Compound 27

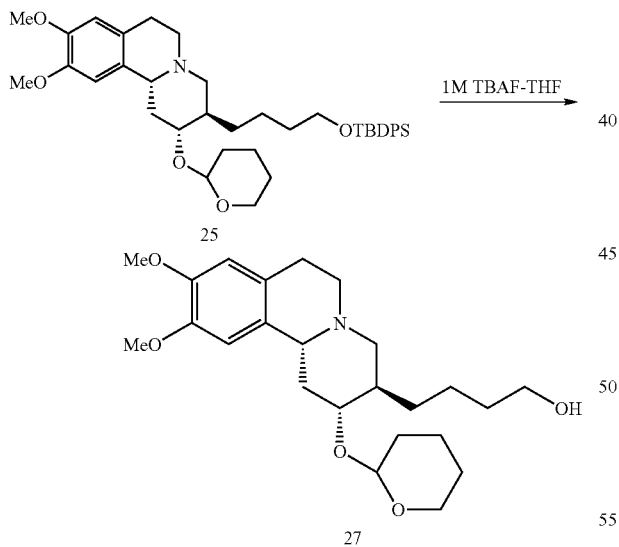

To a 0.3 M solution of the protected dihydrotetrabenazine compound 25 in THF was added a 1.0 M tetrabutylammonium fluoride (TBAF) solution in THF (3.3 eq) bringing the final reaction concentration to 0.15 M with respect to the starting material 25. The reaction mixture was allowed to continue stirring at room temperature for 14 h. The mixture was diluted with deionized water, and extracted with three portions of dichloromethane. The combined organic extracts were dried ($MgSO_4$), filtered, and concentrated under reduced pressure to provide a yellow oil. The crude material was purified by column chromatography on $SiO_2$ (1% triethylamine-DCM to 1% triethyamine-10% methanol-89% DCM; elution was observed at 284 nm and 240 nm). The product alpha-hydroxyalkyl protected dihydrotetrabenazine compound 27 eluted late in the run as a broad peak. The product was a 1:1 mixture of diastereomers that presented as a pale yellow oil 60%: $^1$H NMR ($CD_2Cl_2$) δ 1.11-1.33 (m, 2.0H), 1.48-1.66 (m, 8.0H), 1.69-1.80 (m, 2.5H), 1.81-1.95 (1.5H), 1.98-2.13 (m, 1.0H), 2.21-2.38 (m, 1.0H), 2.40-2.52 (m, 1.0H), 2.58-2.67 (m, 1.5H), 2.70 (ddd, J=12.5, 3.8, 2.5 Hz, 0.5H), 2.95-3.15 (m, 4.0H), 3.33 (ddd, J=9.5, 9.5, 4.5 Hz, 0.5H), 3.51-3.59 (m, 1.5H), 3.62 (apparent dd, J=9.7, 6.3 Hz, 2.0H), 3.81 (apparent s, 4.5H), 3.82 (s, 1.5H), 3.82-3.96 (m, 0.5H), 3.97-4.04 (m, 0.5H), 4.69 (dd, J=3.6, 2.8 Hz, 0.5H), 4.89-4.94 (m, 0.5H), 6.60 (apparent d, J=1.8 Hz, 1.0H), 6.70 (apparent d, J=3.5 Hz, 1.0H); $^{13}$C NMR ($CD_2Cl_2$) δ 19.99, 20.19, 22.91, 23.16, 25.64, 25.66, 29.28, 29.32, 29.71, 29.78, 31.13, 31.32, 33.13, 33.24, 35.96, 39.35, 41.38, 42.32, 51.66, 51.85, 55.74, 56.01, 56.16, 59.82, 59.93, 60.68, 60.95, 62.32, 62.55, 62.83, 62.86, 75.96, 82.35, 94.72, 101.75, 108.71, 108.74, 111.71, 111.78, 126.71, 126.89, 129.78, 129.82, 147.34, 147.37, 147.69, 147.73; LRMS-(ESI+) calcd for ($C_{24}H_{37}NO_5$+H) [M+H]$^+$ 448.31, found 448.25.

Method 21 Preparation of Alpha-Hydroxyalkyl Protected Dihydrotetrabenazine Compound 28

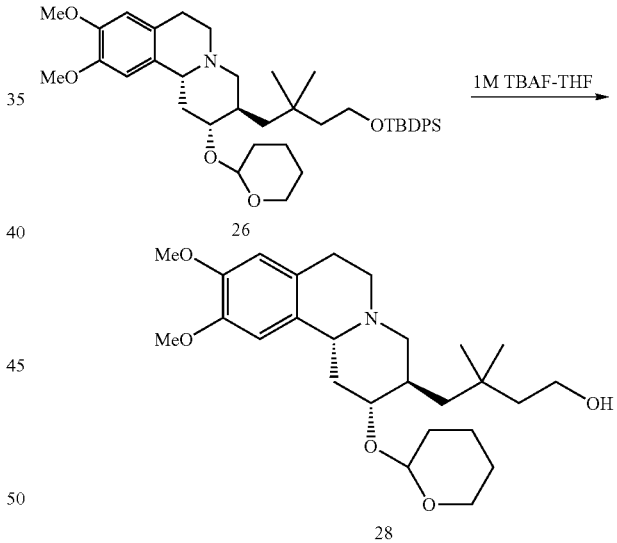

To a 0.3 M solution of the doubly protected dihydrotetrabenazine compound 26 in THF was added a 1.0 M TBAF solution in THF (3.3 eq) bringing the final reaction concentration to 0.15 M with respect to the starting material 26. The reaction mixture was allowed to continue stirring at room temperature for 14 h. The mixture was diluted with deionized water, and extracted with three portions of dichloromethane. The combined organic extracts were dried ($MgSO_4$), filtered, and concentrated under reduced pressure to provide a yellow oil. The crude material was purified by column chromatography on $SiO_2$ (1% triethylamine-DCM to 1% triethyamine-10% methanol-89% DCM; elution was observed at 284 nm and 240 nm). The product eluted late in the run as a broad peak. The product alpha-hydroxyalkyl protected dihydrotetrabenazine compound 28 was a 1:1 mixture of diastereomers that presented as a colorless oil 71%: $^1$H NMR (CD$_2$Cl$_2$) δ 0.90-1.10 (m, 6.5H), 1.23-1.39 (m, 0.5H), 1.48-1.69 (m, 7.0H), 1.71-1.94 (m, 4.0H), 2.08 (m, 1.0H), 2.38-2.83 (m, 4.0H), 2.93-3.16 (m, 3.5H), 3.22 (ddd, J=9.5, 9.5, 4.5 Hz, 0.5H), 3.40-3.60 (m, 1.5H), 3.61-3.76 (m, 2.0H), 3.77-3.91 (m, 6H), 3.92-4.06 (m, 1.5H), 4.62-4.83 (m, 0.5H), 4.83-5.09 (m, 0.5H), 6.60 (apparent d, J=1.8 Hz, 1.0H), 6.70 (apparent d, J=3.5 Hz, 1.0H); $^{13}$C NMR (CD$_2$Cl$_2$) δ 19.96, 25.67, 27.62, 27.71, 27.89, 29.26, 29.30, 31.18, 31.28, 32.78, 35.87, 37.52, 38.28, 39.34, 41.47, 41.95, 45.18, 45.29, 51.50, 51.74, 55.72, 55.99, 56.15, 59.12, 59.19, 60.60, 60.85, 62.58, 62.71, 62.82, 62.94, 76.16, 83.14, 94.56, 102.07, 108.75, 111.73, 111.81, 126.69, 126.86, 129.86, 129.93, 147.33, 147.37, 147.67, 147.73; LRMS-(ESI+) calcd for (C$_{26}$H$_{41}$NO$_5$+H) [M+H]$^+$ 448.31. found 448.25.

Method 22 Preparation of Alpha-Fluoroalkyl Protected Dihydrotetrabenazine Compound 29

6.0H), 1.99-2.12 (m, 1.0H), 2.39-2.51 (m, 1.0H), 2.59-2.67 m, 1.5H), 2.71 (ddd, J=12.5, 3.8, 2.5 Hz, 0.5H), 2.93-3.15 (m, 4.0H), 3.33 (ddd, J=9.3, 9.3, 4.5 Hz, 0.5H), 3.49-3.59 (m, 1.5H), 3.76-3.87 (m, 6.0H), 3.88-3.94 (m, 0.5H), 3.97-4.04 (m, 0.5H), 4.42 (ddd, J=6.1, 4.3, 6.1 Hz, 1.0H), 4.54 (ddd, J=6.1, 4.3, 6.1 Hz, 1.0H), 4.66-4.74 (m, 0.5H), 4.91-4.99 (m, 0.5H), 6.56-6.66 (m, 1.0H), 6.68-6.78 (m, 1.0H); $^{13}$C NMR (CD$_2$Cl$_2$) δ 19.79, 20.22, 22.60, 22.63, 22.66, 22.69, 25.66, 25.72, 29.42, 29.46, 29.65, 29.76, 30.73, 30.79, 30.92, 30.98, 31.15, 31.25, 36.02, 39.50, 41.57, 42.41, 51.75, 51.93, 55.76, 56.04, 56.17, 59.88, 59.96, 60.70, 60.97, 62.49, 62.89, 75.83, 82.45, 83.39, 83.49, 85.01, 85.12, 94.29, 101.76, 108.75, 108.79, 111.75, 111.82, 126.83, 126.99, 129.96, 130.01, 147.35, 147.38, 147.67, 147.72; LRMS-(ESI+) calcd for (C$_{24}$H$_{36}$FNO$_4$$^+$H) [M+H]$^+$ 422.27, found 422.23.

Method 23 Preparation of Alpha-Fluoroalkyl Protected Dihydrotetrabenazine Compound 30

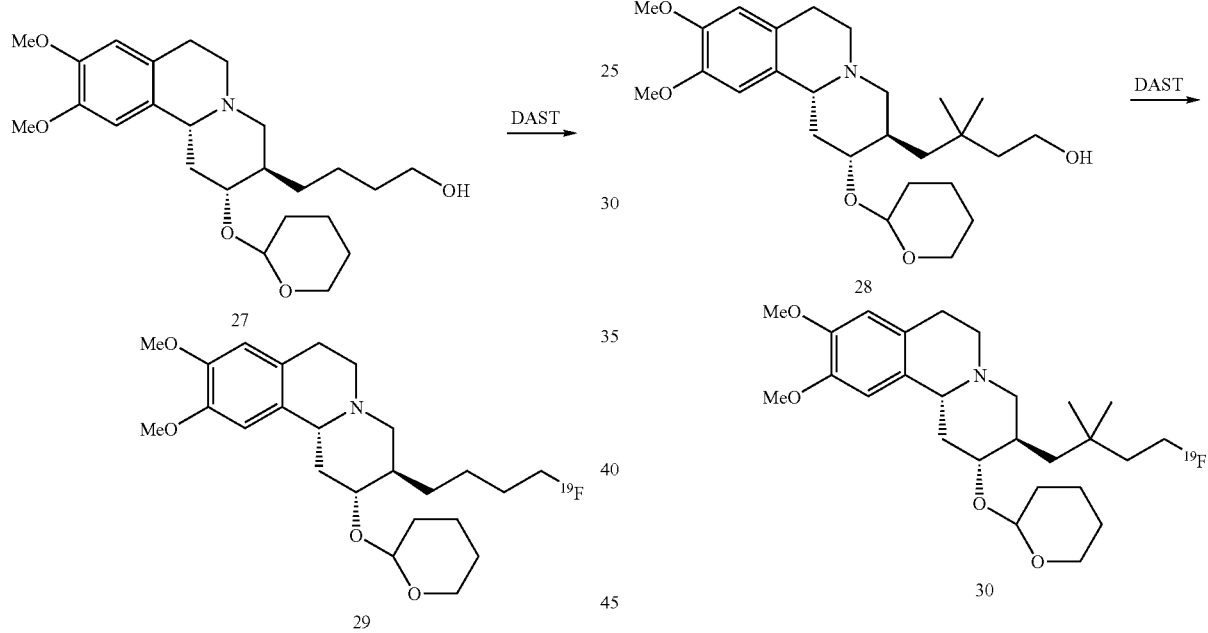

To a 60 mM solution of the starting alpha-hydroxyalkyl protected dihydrotetrabenazine compound 27 in dichloromethane was added diethylaminosulfur trifluoride (DAST, 2.2 eq.) at room temperature. The reaction was stirred for 14 h at this temperature, and then quenched by the addition of saturated aqueous potassium carbonate solution. The aqueous and organic layers were partitioned, and the aqueous layer was extracted with two portions of dichloromethane. The combined organic extracts were dried (MgSO$_4$), filtered, and concentrated under reduced pressure to provide an orange oil that was purified by flash chromatography on SiO$_2$ (1% triethylamine-DCM to 1% triethyamine-10% methanol-89% DCM, 40 CV; elution was observed at 284 nm and 240 nm). The desired product eluted as a broad peak, late in the run. The product alpha-fluoroalkyl protected dihydrotetrabenazine compound 29 was a pale yellow oil that existed as a 1:1 mixture of diastereomers 58%: $^1$H NMR (CD$_2$Cl$_2$) δ 1.12-1.31 (m, 2.0H), 1.50-1.67 (m, 6.0H), 1.66-1.91 (m, To a 60 mM solution of the starting alpha-hydroxyalkyl protected dihydrotetrabenazine compound 28 in dichloromethane was added diethylaminosulfur trifluoride (DAST, 2.2 eq.) at room temperature. The reaction was stirred for 14 h at this temperature, and then quenched by the addition of saturated aqueous potassium carbonate solution. The aqueous and organic layers were partitioned, and the aqueous layer was extracted with two portions of dichloromethane. The combined organic extracts were dried (MgSO$_4$), filtered, and concentrated under reduced pressure to provide an orange oil that was purified by flash chromatography on SiO$_2$ (1% triethylamine-DCM to 1% triethyamine-10% methanol-89% DCM, 40CV; elution was observed at 284 nm and 240 nm). The desired product eluted as a broad peak, late in the run. The product alpha-fluoroalkyl protected dihydrotetrabenazine compound 30 was an oil that existed as a 1:1 mixture of diastereomers 46%. The isolated material was taken on to the next step without additional characterization or analysis.

Example 2

Preparation of Alpha-Fluoroalkyl Dihydrotetrabenazine Compound 31

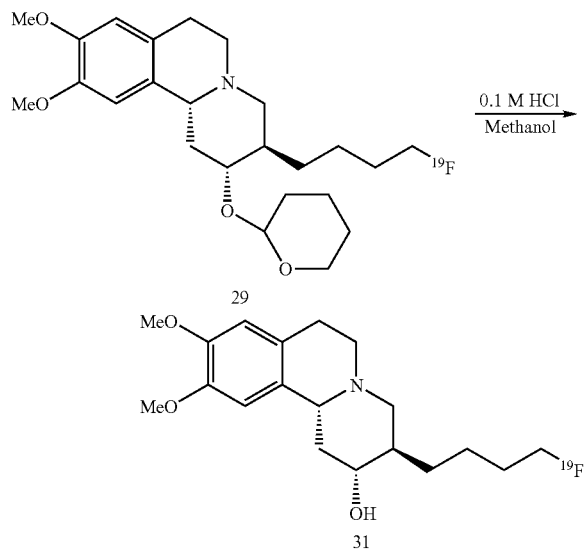

The starting material, alpha-fluoroalkyl protected dihydrotetrabenazine compound 29, was dissolved in 0.1 M HCl in MeOH to provide a 26 mM solution of the starting material 29. The reaction mixture was permitted to stir for 1.5 h at room temperature. The solvent was removed under reduced pressure, and the residue was dried under high vacuum for one hour. The residue was treated with aqueous potassium carbonate solution and extracted with three portions of dichloromethane. The dichloromethane extracts were dried, (MgSO$_4$) filtered, and concentrated under reduced pressure to provide the desired product alpha-fluoroalkyl dihydrotetrabenazine 31 as a colorless solid 99%: $^1$H NMR (CD$_2$Cl$_2$) δ 1.15-1.26 (m, 1H), 1.47 (m, 2H), 1.54-1.91 (m, 6H), 2.05 (apparent t, J=11.4 Hz, 1H), 2.43-2.51 (m, 1H), 2.56 (ddd, J=12.3, 3.8, 2.5 Hz, 1H), 2.60-2.68 (m, 1H), 2.96-3.09 (m, 3H), 3.15 (apparent d, J=11.1 Hz, 1H), 3.42 (ddd, J=9.5, 9.5, 4.6 Hz, 1H), 3.81 (s, 6H), 4.42 (t, J=6.1 Hz, 1H), 4.54 (t, J=6.1 Hz, 1H), 6.61 (s, 1H), 6.70 (s, 1H); $^{13}$C NMR (CD$_2$Cl$_2$) δ 22.80 (d$_{C^*-C-C-F}$, J=5.1 Hz), 29.41, 29.80, 30.99 (d$_{C^*-C-F}$, J=19.0 Hz), 41.02, 43.91, 51.93, 55.90, 56.07, 59.79, 61.05, 74.00, 84.36 (d$_{C^*-F}$, J=163.2 Hz), 108.58, 111.88, 126.79, 129.68, 147.55, 147.82; LRMS-(ESI+) calcd for (C$_{19}$H$_{28}$FNO$_3$+H) [M+H]$^+$ 338.21. found 338.20.

Example 3

Preparation of Alpha-Fluoroalkyl Dihydrotetrabenazine Compound 32

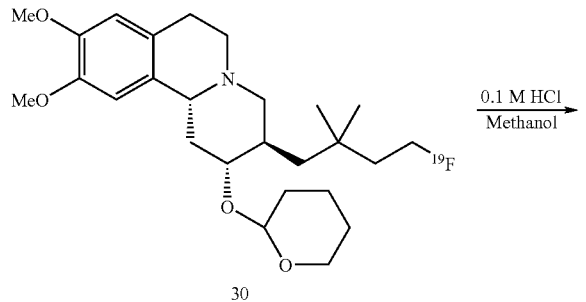

The starting material was dissolved in 0.1 M HCl in MeOH to provide a 26 mM solution of the starting material 30. The reaction mixture was permitted to stir for 1.5 h at room temperature. The solvent was removed under reduced pressure, and the residue was dried under high vacuum for one hour. The residue was treated with aqueous potassium carbonate solution and extracted with three portions of dichloromethane. The dichloromethane extracts were dried, (MgSO$_4$) filtered, and concentrated under reduced pressure to provide the desired product alpha-fluoroalkyl dihydrotetrabenazine 32 as colorless solid 99%: $^1$H NMR (CD$_2$Cl$_2$) δ 0.92-0.97 (m, 1H), 1.01 (s, 6H), 1.03-1.11 (m, 1H), 1.42 (q, J=11.4 Hz, 1H), 1.62-1.85 (m, 1H), 2.06 (t, J=11.4 Hz, 1H), 2.39-2.49 (m, 1H), 2.57 (ddd, J=12.3, 3.8, 2.5 Hz, 1H), 2.60-2.68 (m, 1H), 2.94-3.08 (m, 3H), 3.14 (apparent d, J=11.1 Hz, 1H), 3.33 (ddd, J=9.5, 9.5, 4.6 Hz, 1H), 3.81 (s, 6H), 4.54 (ddd, 6.2, 6.2, 2.0 Hz, 1H), 4.66 (ddd, 6.2, 6.2, 1.8 Hz, 1H), 6.60 (s, 1H), 6.69 (s, 1H); $^{13}$C NMR (CD$_2$Cl$_2$) δ 27.47, 27.65, 29.33, 32.65 (d$_{C^*-C-C-F}$, J=4.4 Hz), 40.09, 40.87, 42.07 (d$_{C^*-C-F}$, J=17.6 Hz), 42.09, 51.75, 55.78, 55.94, 60.94, 62.64, 74.09, 82.16 (d$_{C^*-F}$, J=161.7 Hz), 108.40, 111.76, 126.69, 129.73, 147.42, 147.66; HRMS-(ESI+) calcd for (C$_{21}$H$_{32}$FNO$_3$+H) [M+H]$^+$ 366.24445. found 366.24404.

Example 4

Preparation of Fluorophilic Protected Tetrabenazine Tosylate 33 Via Intermediate Protected Tetrabenazine Alcohol 20

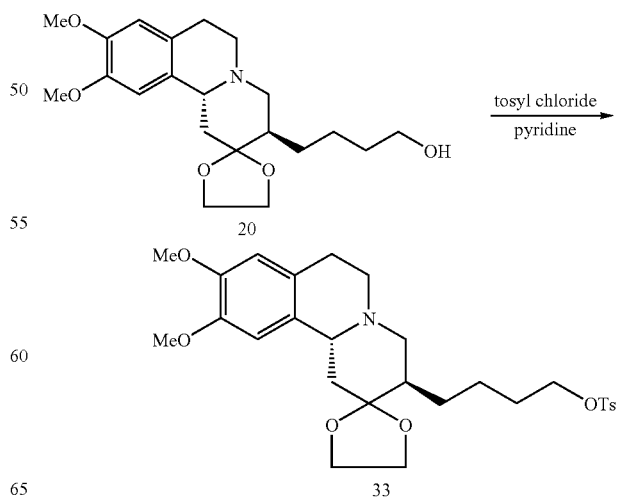

To a solution of alpha-hydroxyalkyl protected TBZ compound 20 in pyridine is added toluene sulfonyl chloride (tosyl chloride 1.5 equivalents) and the mixture is stirred at 0° C. and periodically monitored by thin layer chromatography (tlc). When tlc indicates complete consumption of the starting alcohol 20, the reaction mixture is quenched by adding ice-cold water and EtOAc. The organic layer is washed successively with water, 1M HCl (5×), saturated Na$_2$CO$_3$ and brine. The organic layer is dried over anhydrous Na$_2$SO$_4$, filtered and concentrated under reduced pressure. The residue is chromatographed on silica gel to afford fluorophilic protected TBZ tosylate 33.

Example 5

Preparation of Fluorophilic Protected Tetrabenazine Tosylate 34 Via Intermediate Protected Tetrabenazine Alcohol 27

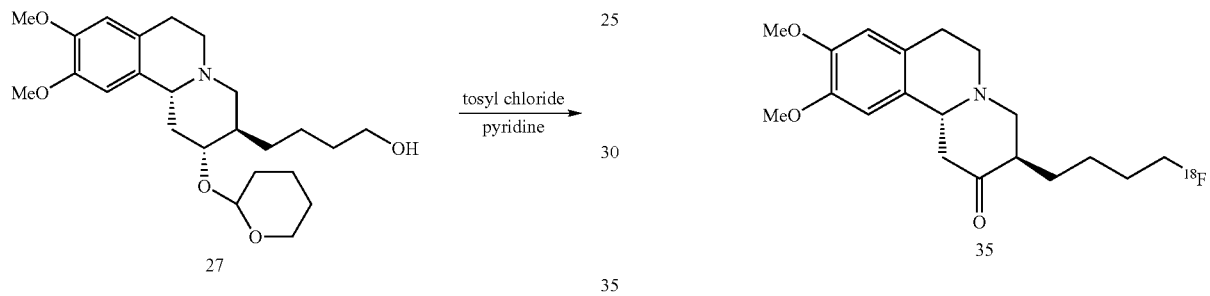

To a solution of alpha-hydroxyalkyl protected TBZ compound 27 in pyridine is added toluene sulfonyl chloride (tosyl chloride 1.5 equivalents) and the mixture is stirred at 0° C. and periodically monitored by thin layer chromatography (tlc). When tlc indicates complete consumption of the starting alcohol 20, the reaction mixture is quenched by adding ice-cold water and EtOAc. The organic layer is washed successively with water, 1M HCl (5×), saturated Na$_2$CO$_3$ and brine. The organic layer is dried over anhydrous Na$_2$SO$_4$, filtered and concentrated under reduced pressure. The residue is chromatographed on silica gel to afford fluorophilic protected TBZ tosylate 34.

Example 6

Preparation of PET Imaging Agent 35

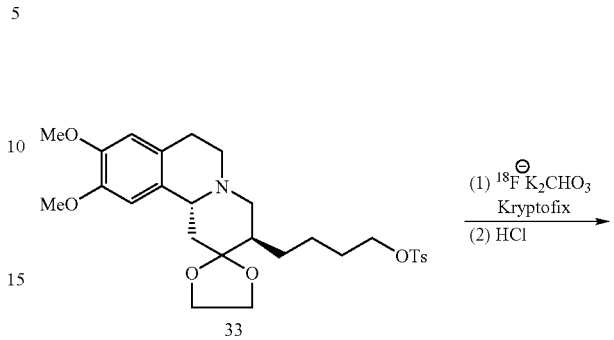

To a Teflon-lined reaction vial contained in a shielded hood and fitted with a nitrogen purge inlet and magnetic spin bar, is added about 1 milliliter of an aqueous acetonitrile solution F-18 fluoride ion, potassium carbonate (about 1 mg), and Kryptofix 221 (about 10 mg). The vial is heated at 100° C. under a stream of nitrogen to effect the azeotropic removal of water. Additional dry acetonitrile (1 mL) is added and evaporated. This azeotropic drying protocol is repeated three times. After the final evaporation step a mixture of dimethyl formamide and acetonitrile (about 1 mL) containing fluorophilic protected TBZ tosylate 33 (2 mg) is added and the vial is sealed. The reaction mixture is stirred and heated at 100° C. for 10 minutes and then is cooled to room temperature. The product mixture comprising the starting tosylate 33 and the product F-18 alpha-fluoroalkyl protected tetrabenazine is diluted with water (10 mL) and applied to a Sep-Pak cartridge. The cartridge is then washed with water (3×) to remove unreacted fluoride ion and other water soluble components of the product mixture. The radiolabled alpha-fluoroalkyl protected tetrabenazine compound and starting tosylate 33 are then eluted from the cartridge with acetonitrile. Most of the acetonitrile is then evaporated and the residue is dissolved in aqueous methanol containing hydrochloric acid (HCl) and heated at 60° C. The mixture is again concentrated and subjected to preparative reverse phase HPLC to afford an aqueous formulation comprising PET imaging agent 35.

Example 7

Preparation of PET Imaging Agent 36

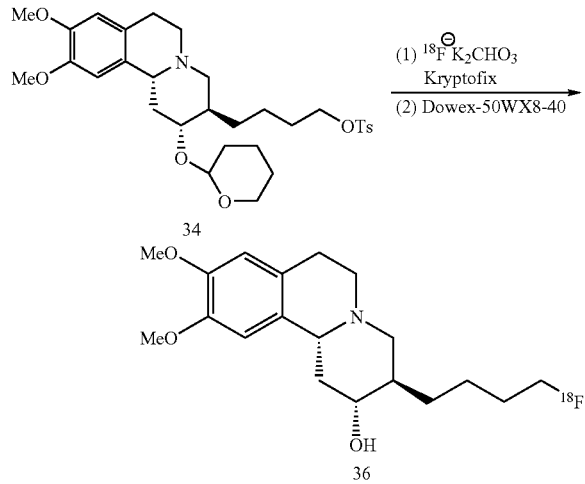

To a Teflon-lined reaction vial contained in a shielded hood and fitted with a nitrogen purge inlet and magnetic spin bar, is added about 1 milliliter of an aqueous acetonitrile solution F-18 fluoride ion, potassium carbonate (about 1 mg), and Kryptofix 221 (about 10 mg). The vial is heated at 100° C. under a stream of nitrogen to effect the azeotropic removal of water. Additional dry acetonitrile (1 mL) is added and evaporated. This azeotropic drying protocol is repeated three times. After the final evaporation step a mixture of dimethyl formamide and acetonitrile (about 1 mL) containing fluorophilic protected DTBZ tosylate 34 (2 mg) is added and the vial is sealed. The reaction mixture is stirred and heated at 100° C. for 10 minutes and then is cooled to room temperature. The product mixture comprising the starting tosylate 34 and the intermediate F-18 alpha-fluoroalkyl protected dihydrotetrabenazine is diluted with water (10 mL) and applied to a Sep-Pak cartridge. The cartridge is then washed with water (3×) to remove unreacted fluoride ion and other water soluble components of the product mixture. The radiolabled alpha-fluoroalkyl intermediate and starting tosylate 34 are then eluted from the cartridge with acetonitrile. Most of the acetonitrile is then evaporated and the residue is dissolved in aqueous acetonitrile and treated with DOWEX strongly acidic cation exchange resin at 65° C. for 10 minutes. The reaction mixture is then filtered and subjected to preparative reverse phase HPLC to afford an aqueous formulation comprising PET imaging agent 36.

Example 8

Alternate Preparation of PET Imaging Agent 36

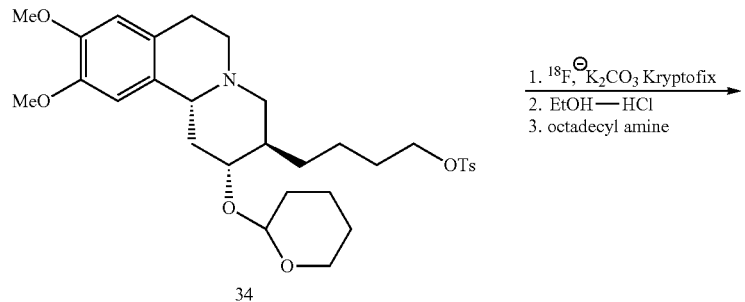

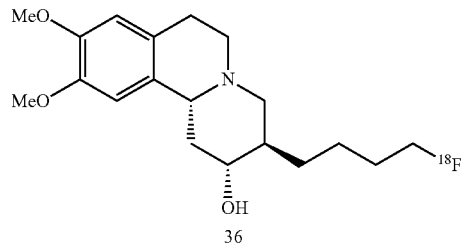

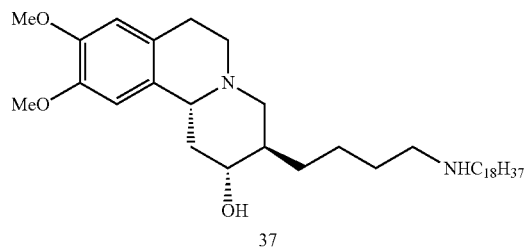

To a Teflon-lined reaction vial contained in a shielded hood and fitted with a nitrogen purge inlet and magnetic spin bar, is added about 1 milliliter of an aqueous acetonitrile solution F-18 fluoride ion, potassium carbonate (about 1 mg), and Kryptofix 221 (about 10 mg). The vial is heated at 100° C. under a stream of nitrogen to effect the azeotropic removal of water. Additional dry acetonitrile (1 mL) is added and evaporated. This azeotropic drying protocol is repeated three times. After the final evaporation step a mixture of dimethyl formamide and acetonitrile (about 1 mL) containing fluorophilic tosylate 34 (2 mg) is added and the vial is sealed. The reaction mixture is stirred and heated at 100° C. for 10 minutes and then is cooled to room temperature. The product mixture comprising the starting tosylate 34 and the product F-18 alpha-fluoroalkyl protected dihydrotetrabenazine intermediate is concentrated under a stream of nitrogen and the residue is dissolved in ethanol containing HCl and the mixture is warmed briefly to effect removal of the THP protecting group. Excess octadecyl amine (5 mg) and potassium carbonate (2 mg) are then added and the mixture is heated for 5 minutes at 60° C. to convert unreacted tosylate groups to the corresponding octadecyl amine. The product mixture is then diluted with water (10 mL) and applied to a Sep-Pak cartridge. The cartridge is then washed with water (3×) to remove unreacted fluoride ion and other water soluble components of the product mixture. The radiolabled alpha-fluoroalkyl compound 36 and the corresponding octadecyl amine adduct 37 are then eluted from the cartridge with acetonitrile. Most of the acetonitrile is then evaporated and the residue is dissolved in aqueous acetonitrile and subjected to preparative reverse phase HPLC to provide purified PET imaging agent 36.

Measurement of Binding Affinity of Alpha-fluoroalkyl Compounds to VMAT-2

VMAT-2 binding affinities were measured for alpha-fluoroalkyl dihydrotetrabenazine compounds 31, 32, and 2-epi-32 provided by the present invention. VMAT-2 binding affinity measurements were carried out by Novascreen Biosciences Corporation (Hanover, Md., USA) using protocol Cat. No. 100-0751. Novascreen, Inc. is a commercial provider of biological assays for the pharmaceutical industry. Binding affinity data are presented in Table 15 and illustrate very high binding affinity for the alpha-fluoroalkyl compounds of the present invention relative to a DTBZ control (Comparative Example 1). The data obtained for alpha-fluoroalkyl compounds 31, 32 and 2-epi-32 reveal an unexpected tolerance of fluoroalkyl substitution at ring position-3, a structural change relative to TBZ and DTBZ which combines a change in the size and lipophilicity of the group at ring position-3 with the uncertainty which arises whenever a hydrogen in a biologically active molecule is replaced by fluorine. In addition, the binding constants Ki expressed in nano-molar (nM) concentration units indicate a very high affinity of the alpha-fluoroalkyl compounds of the present invention for the VMAT-2 biomarker.

TABLE 15

VMAT-2 Binding Affinity of Alpha-Fluoroalkyl Compounds 31, 32 and 2-epi-32

| Example No. | Compound No. | Structure | Ki (nM) |
|---|---|---|---|
| Example 9 | 31 | [structure of compound 31] | 6.4 |
| Example 10 | 2-epi-32 | [structure of compound 2-epi-32] | 2.6 |
| Example 11 | 32 | [structure of compound 32] | 0.45 |

TABLE 15-continued

VMAT-2 Binding Affinity of Alpha-Fluoroalkyl
Compounds 31, 32 and 2-epi-32

| Example No. | Compound No. | Structure | Ki (nM) |
|---|---|---|---|
| Comparative Example 1 | DTBZ (18) | 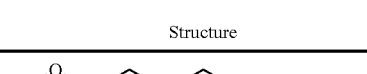 | 3.0 |

The foregoing examples are merely illustrative, serving to illustrate only some of the features of the invention. The appended claims are intended to claim the invention as broadly as it has been conceived and the examples herein presented are illustrative of selected embodiments from a manifold of all possible embodiments. Accordingly, it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied, those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

What is claimed is:

1. A fluorophilic compound having structure VII

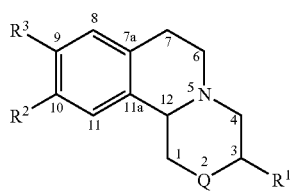

(VII)

wherein Q is a carbonyl group, a protected carbonyl group, a hydroxy methine group, or a protected hydroxy methine group; $R^1$ is a $C_1$-$C_{20}$ aliphatic, $C_2$-$C_{20}$ cycloaliphatic, or $C_2$-$C_{20}$ aromatic radical comprising at least one functional group susceptible to reaction with nucleophilic fluoride ion, said functional group being selected from the group consisting of aliphatic sulfonate esters, and aromatic sulfonate esters; $R^2$ is hydrogen, a $C_1$-$C_{10}$ alkyl group or a $C_1$-$C_{10}$ alkoxy group; and $R^3$ is hydrogen, a $C_1$-$C_{10}$ alkyl group or a $C_1$-$C_{10}$ alkoxy group.

2. The fluorophilic compound according to claim 1, which is enantiomerically enriched.

3. The fluorophilic compound according to claim 2, which is comprised of at least 95 mole % of an enantiomer having the R configuration at ring position-12.

4. The fluorophilic compound according to claim 2, which is comprised of at least 95 mole % of an enantiomer having the R configuration at ring position-3.

5. The fluorophilic compound according to claim 2, wherein Q is a protected ketone group.

6. The fluorophilic compound according to claim 2, wherein Q is a protected hydroxy methine group.

7. The fluorophilic compound according to claim 2, wherein $R^1$ comprises at least one aromatic sulfonate ester group.

8. The fluorophilic compound according to claim 2, wherein $R^1$ comprises at least one aliphatic sulfonate ester group.

9. The fluorophilic compound according to claim 8, which is enantiomerically enriched.

10. The fluorophilic compound according to claim 9, which is comprised of at least 95 mole % of an enantiomer having the R configuration at ring position-12.

11. The fluorophilic compound according to claim 9, in which the group —$R^1$ at ring position-3 has a syn configuration relative to the hydrogen at ring position-12.

12. The fluorophilic compound according to claim 9, wherein Q is a protected ketone group.

13. The fluorophilic compound according to claim 8, wherein $R^1$ comprises at least one carbon-carbon double bond.

14. The fluorophilic compound according to claim 8, wherein $R^1$ comprises at least one carbon-carbon triple bond.

15. An enantiomerically enriched fluorophilic compound comprising a principal component enantiomer having structure VIII

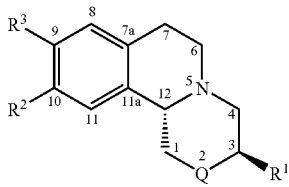

(VIII)

wherein Q is a carbonyl group, a protected carbonyl group, a hydroxy methine group, or a protected hydroxy methine group; $R^1$ is a $C_1$-$C_{20}$ aliphatic, $C_2$-$C_{20}$ cycloaliphatic, or $C_2$-$C_{20}$ aromatic radical comprising at least one functional group susceptible to reaction with nucleophilic fluoride ion, said functional group being selected from the group consisting of aliphatic sulfonate esters, and aromatic sulfonate esters; $R^2$ is hydrogen, a $C_1$-$C_{10}$ alkyl group or a $C_1$-$C_{10}$ alkoxy group; and $R^3$ is hydrogen, a $C_1$-$C_{10}$ alkyl group or a $C_1$-$C_{10}$ alkoxy group.

16. The enantiomerically enriched fluorophilic compound according to claim 15, which is comprised of at least 80 mole % of an enantiomer having structure VIII.

17. The enantiomerically enriched fluorophilic compound according to claim 15, which is comprised of at least 95 mole % of an enantiomer having structure VIII.

18. An enantiomerically enriched fluorophilic compound comprising a principal component enantiomer having structure IX

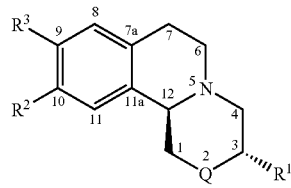

(IX)

wherein Q is a carbonyl group, a protected carbonyl group, a hydroxy methine group, or a protected hydroxy methine group; $R^1$ is a $C_1$-$C_{20}$ aliphatic, $C_2$-$C_{20}$ cycloaliphatic, or $C_2$-$C_{20}$ aromatic radical comprising at least one functional group susceptible to reaction with nucleophilic fluoride ion, said functional group being selected from the group consisting of aliphatic sulfonate esters, and aromatic sulfonate esters; $R^2$ is hydrogen, a $C_1$-$C_{10}$ alkyl group or a $C_1$-$C_{10}$ alkoxy group; and $R^3$ is hydrogen, a $C_1$-$C_{10}$ alkyl group or a $C_1$-$C_{10}$ alkoxy group.

19. The enantiomerically enriched fluorophilic compound according to claim 18, which is comprised of at least 95 mole % of an enantiomer having structure IX.

* * * * *

UNITED STATES PATENT AND TRADEMARK OFFICE
CERTIFICATE OF CORRECTION

PATENT NO. : 7,910,738 B2  
APPLICATION NO. : 11/947275  
DATED : March 22, 2011  
INVENTOR(S) : Rishel et al.

Page 1 of 2

It is certified that error appears in the above-identified patent and that said Letters Patent is hereby corrected as shown below:

In Column 37, in Table "14-continued", Lines 6-13, in structure "14c",

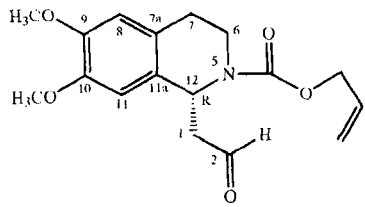 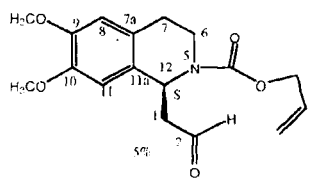

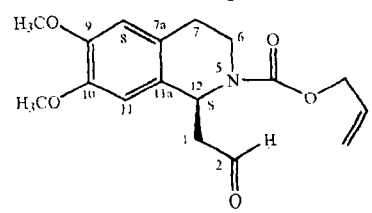 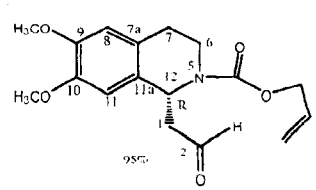

delete " " and insert -- --, therefor.

In Column 39, Line 21, delete "hydrolyis" and insert -- hydrolysis --, therefor.

In Column 46, Line 31, delete "418.2594." and insert -- 418.2594, --, therefor.

In Column 48, Line 33, delete "600.3509." and insert -- 600.3509, --, therefor.

In Column 50, Line 67, delete "572.3196." and insert -- 572.3196, --, therefor.

In Column 53, Line 5, delete "320.2226." and insert -- 320.2226, --, therefor.

In Column 55, Line 53, delete "336.20." and insert -- 336.20, --, therefor.

In Column 56, Line 26, delete "(m, 1H)," and insert -- (m, 11H), --, therefor.

Signed and Sealed this  
Twenty-eighth Day of June, 2011

David J. Kappos  
*Director of the United States Patent and Trademark Office*

CERTIFICATE OF CORRECTION (continued)
U.S. Pat. No. 7,910,738 B2

In Column 57, Line 27, delete "(ddd, J=11.4, 11.4, 3.9 Hz," and insert -- (ddd, J=11.4, 3.9 Hz, --, therefor.

In Column 57, Line 49, delete "448.31." and insert -- 448.31, --, therefor.

In Column 61, Line 18, delete "448.31." and insert -- 448.31, --, therefor.

In Column 63, Line 48, delete "338.21." and insert -- 338.21, --, therefor.

In Column 64, Line 36, delete "366.24445." and insert -- 366.24445, --, therefor.